US010631724B2

(12) United States Patent
Neal et al.

(10) Patent No.: US 10,631,724 B2
(45) Date of Patent: Apr. 28, 2020

(54) METHOD AND SYSTEM FOR DYNAMICALLY MEASURING TEAR FILM BREAKUP AND IRREGULARITY USING CORNEAL TOPOGRAPHY AND WAVEFRONT ABERROMETRY

(71) Applicant: AMO WaveFront Sciences, LLC, Santa Ana, CA (US)

(72) Inventors: Daniel R. Neal, Tijeras, NM (US); Richard J. Copland, Albuquerque, NM (US); Jason Hoy, Albuquerque, NM (US); Wei Xiong, Albuquerque, NM (US)

(73) Assignee: AMO Development, LLC, Santa Ana, CA (US)

( * ) Notice: Subject to any disclaimer, the term of this patent is extended or adjusted under 35 U.S.C. 154(b) by 52 days.

(21) Appl. No.: 15/902,933

(22) Filed: Feb. 22, 2018

(65) Prior Publication Data

US 2018/0235460 A1 Aug. 23, 2018

Related U.S. Application Data

(60) Provisional application No. 62/462,269, filed on Feb. 22, 2017.

(51) Int. Cl.
| | |
|---|---|
| *A61B 3/10* | (2006.01) |
| *A61B 3/107* | (2006.01) |
| *A61B 3/14* | (2006.01) |
| *A61B 3/00* | (2006.01) |
| *A61B 3/103* | (2006.01) |

(52) U.S. Cl.
CPC ............. *A61B 3/101* (2013.01); *A61B 3/107* (2013.01); *A61B 3/14* (2013.01); *A61B 3/0033* (2013.01); *A61B 3/103* (2013.01)

(58) Field of Classification Search
CPC .......... A61B 3/101; A61B 3/107; A61B 3/14; A61B 3/103; A61B 3/0033
USPC ........................................ 351/200, 205, 221
See application file for complete search history.

(56) References Cited

U.S. PATENT DOCUMENTS

| | | |
|---|---|---|
| 6,607,274 B2 | 8/2003 | Stantz et al. |
| 7,988,293 B2 | 8/2011 | Raymond et al. |
| 9,504,376 B2 | 11/2016 | Neal et al. |
| 9,706,912 B2 | 7/2017 | Copland et al. |

(Continued)

OTHER PUBLICATIONS

International Search Report and Written Opinion for Application No. PCT/US2018/019284, dated May 14, 2018, 11 pages.

(Continued)

*Primary Examiner* — Tuyen Tra
(74) *Attorney, Agent, or Firm* — Johnson & Johnson Surgical Vision, Inc.

(57) ABSTRACT

An optical measurement instrument performs a series of wavefront measurements to obtain a plurality of sets of wavefront aberrometry data for an eye, and performs a series of corneal topography measurements to obtain a plurality of sets of corneal topography data for the eye. Each set of wavefront aberrometry data is obtained at a corresponding different point in time, and each set of corneal topography data is obtained at a corresponding different point in time. The wavefront aberrometry data and the corneal topography data are processed to produce combined tear film breakup data as a function of time. The combined tear film breakup data may be employed as a metric for evaluating a level of tear film breakup of the eye as a function of time.

29 Claims, 26 Drawing Sheets

(56) References Cited

U.S. PATENT DOCUMENTS

| | | |
|---|---|---|
| 9,757,025 B2 | 9/2017 | Copland et al. |
| 2012/0172854 A1 | 7/2012 | Raymond et al. |
| 2014/0300860 A1 | 10/2014 | Tanaka et al. |
| 2015/0138505 A1 | 5/2015 | Grenon et al. |
| 2016/0073868 A1 | 3/2016 | Raymond et al. |
| 2016/0074125 A1 | 3/2016 | Raymond et al. |
| 2016/0150952 A1 | 6/2016 | Raymond et al. |
| 2017/0027437 A1 | 2/2017 | Neal et al. |
| 2017/0071465 A1 | 3/2017 | Neal et al. |

OTHER PUBLICATIONS

Himebaugh N.L., et al., "Scale and Spatial Distribution of Aberrations Associated With Tear Breakup," Optometry and Vision Science, Optometry and Vision Science, Nov. 2012, vol. 89 (11), pp. 1590-1600.

Khanal S., et al., "Dry Eye Diagnosis, " Investigative Ophthalmology & Visual Science, Apr. 2008, vol. 49 (4), pp. 1407-1414.

Koh S., et al., "Simultaneous Measurement of Tear Film Dynamics Using Wave front Sensor and Optical Coherence Tomography," Investigative Ophthalmology & Visual Science, Jul. 2010, vol. 51 (7), pp. 3441-3448.

Liu H., et al., "Measurement of the Time Course of Optical Quality and Visual Deterioration during Tear Break-Up," Investigative Ophthalmology & Visual Science, Jun. 2010, vol. 51 (6), pp. 3318-3326.

Methodologies to Diagnose and Monitor Dry Eye Disease: Report of the Diagnostic Methodology Subcommittee of the International Dry Eye Workshop (2007), Ocular Surface, Apr. 2007, vol. 5 (2), pp. 108-152.

T=0.8 sec.

T=12.6 sec.

T=.61 sec

T=12.6 sec

T=31.3 sec

T=12.6 sec  #Spots = 281

T=8.4 sec  #Spots = 511

T=.61 sec  #Spots = 923

T=31.3 sec  #Spots = 901
After blink

METHOD AND SYSTEM FOR DYNAMICALLY MEASURING TEAR FILM BREAKUP AND IRREGULARITY USING CORNEAL TOPOGRAPHY AND WAVEFRONT ABERROMETRY

CROSS-REFERENCE TO RELATED APPLICATIONS

This application claims priority to U.S. Provisional Patent Application No. 62/462,269, filed Feb. 22, 2017, which is incorporated hereby by reference in its entirety.

TECHNICAL FIELD

Embodiments of this invention pertain to optical measurement systems and methods, and more particularly, to optical measurement systems and methods which measure tear film breakup of an eye using corneal topography and wavefront aberrometry.

BACKGROUND

Measurement and diagnosis of the tear film of an eye is increasingly important for understanding the corneal condition prior to any surgery or therapy. This information may be used to guide surgery, screen patients or provide appropriate drops or other treatment and in diagnosis of dry eye condition.

A great deal of research has been directed toward methods diagnosing dry eye condition and for measuring tear film or tear film breakup in human eyes. "*Methodologies to Diagnose and Monitor Dry Eye Disease: Report of the Diagnostic Methodology Subcommittee of the International Dry Eye Work Shop* (2007)," 5 THE OCCULAR SURFACE No. 2, April 2007, pp. 108-152 provides a summary of dry eye diagnosis approaches, including slit lamp examination, video recording, and osmolarity analysis. These approaches require a variety of instruments and are sometimes subjective.

Objective measurements of data related to tear film breakup may be analyzed to diagnose dry eye condition. Issues related to such diagnosis include what data should be measured, how the data should be processed for analysis, and what metrics should be employed to gauge the level of tear film breakup for diagnosing a possible dry eye condition.

U.S. Pat. No. 9,504,376, "Optical diagnosis using measurement sequence," issued on 28 Nov. 2016 to Daniel R. Neal et al., and incorporated herein by reference, describes the use of wavefront aberrometry measurement data to evaluate tear film breakup, as does U.S. patent application Ser. No. 15/343,037, filed on 3 Nov. 2016, and also incorporated by reference herein. For example, U.S. Pat. No. 9,504,376 describes how Wavefront Fit Error (WFFE) and wavefront irregularity may be employed to assess potential tear film break up. Additionally, Haixia Liu et al., "*Measurement of the Time Course of Optical Quality and Visual Deterioration during Tear Break-Up*," 51 INVESTIGATIVE OPHTHALMOLOGY & VISUAL SCIENCE No. 6, June 2010, pp. 3318-26 describes some optical metrics of tear quality and retinal image quality which are associated with the decline in vision that occurs with tear film breakup. In particular, Liu et al. describe the use of RMS fit error of wavefront data obtained from wavefront aberrometry measurements as a metric for deterioration of visual quality due to tear film breakup during blink suppression. Further, Nikole L. Himebaugh et al., "*Scale and Spatial Distribution of Optical Aberrations Associated with Tear Break-up*," 89 OPTOMETRY & VISUAL SCIENCE No. 11, November 2012, pp. 1590-1600, concluded that tear film breakup caused by blink suppression may manifest itself as a combination of wavefront aberrations on macroscopic and microscopic scales due to non-uniform tear film thinning and possible exposure of a rough epithelial surface. Each of these documents is incorporated herein by reference.

However, improved methods and systems of measuring data related to tear film breakup, improved systems and methods of processing measured data related to tear film breakup, and improved metrics for quantifying and evaluating tear film breakup based on such measured and processed data are needed.

Accordingly, it would be desirable to provide new systems and method for measuring tear-film breakup.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION

Exemplary embodiments of optical measurement systems and methods for measuring aberrations of an eye to illustrate various aspects and advantages of these devices and methods are described below. However, it should be understood that the principles involved in these devices and methods can be employed in a variety of other contexts, and therefore the novel devices and method disclosed and claimed here should not be construed as being limited to the example embodiments described below.

Figures 1A, 1B:
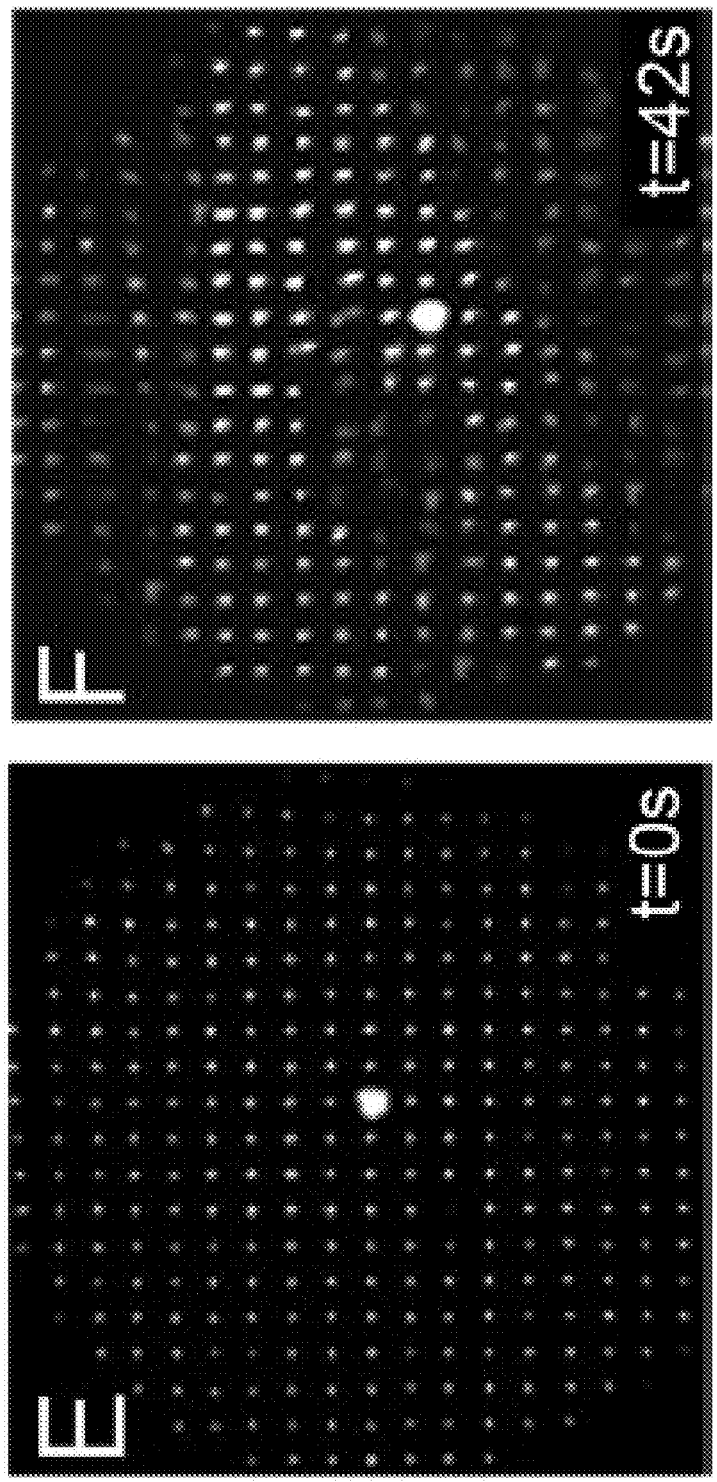
FIGS. 1A and 1B depict Shack-Hartmann wavefront sensor images which illustrate an effect of tear film breakup for an example eye over time.

FIGS. 1A and 1B depict Shack-Hartmann wavefront sensor images from Liu et al. which illustrate an effect of tear film breakup for an example eye over time. In particular, FIG. 1A is a raw image of a Shack-Hartmann wavefront sensor at a point in time immediately following the blink of an eye, and FIG. 1B is a raw image of a Shack-Hartmann wavefront sensor 42 seconds later during which time no subsequent blink occurred.

Figures 2A, 2B:
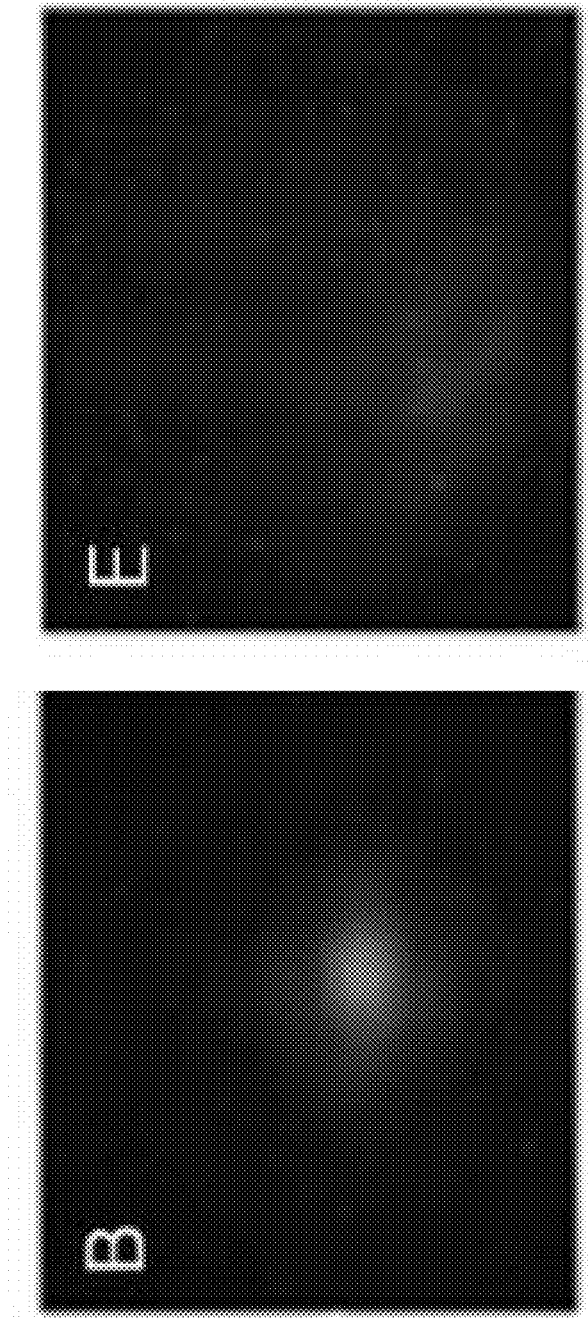
FIGS. 2A and 2B depict spots which have been imaged onto a Shack-Hartmann wavefront sensor from an example eye and which illustrate an effect of tear film breakup over time.

FIGS. 2A and 2B depict spots which have been imaged onto a Shack-Hartmann wavefront sensor from an example eye and which illustrate an effect of tear film breakup over time, as described in Liu et al. Note that the relatively low number of pixels per lenslet for this wavefront sensor system provides little detail for this image. However, the spot degradation after breakup is apparent.

Figure 3:
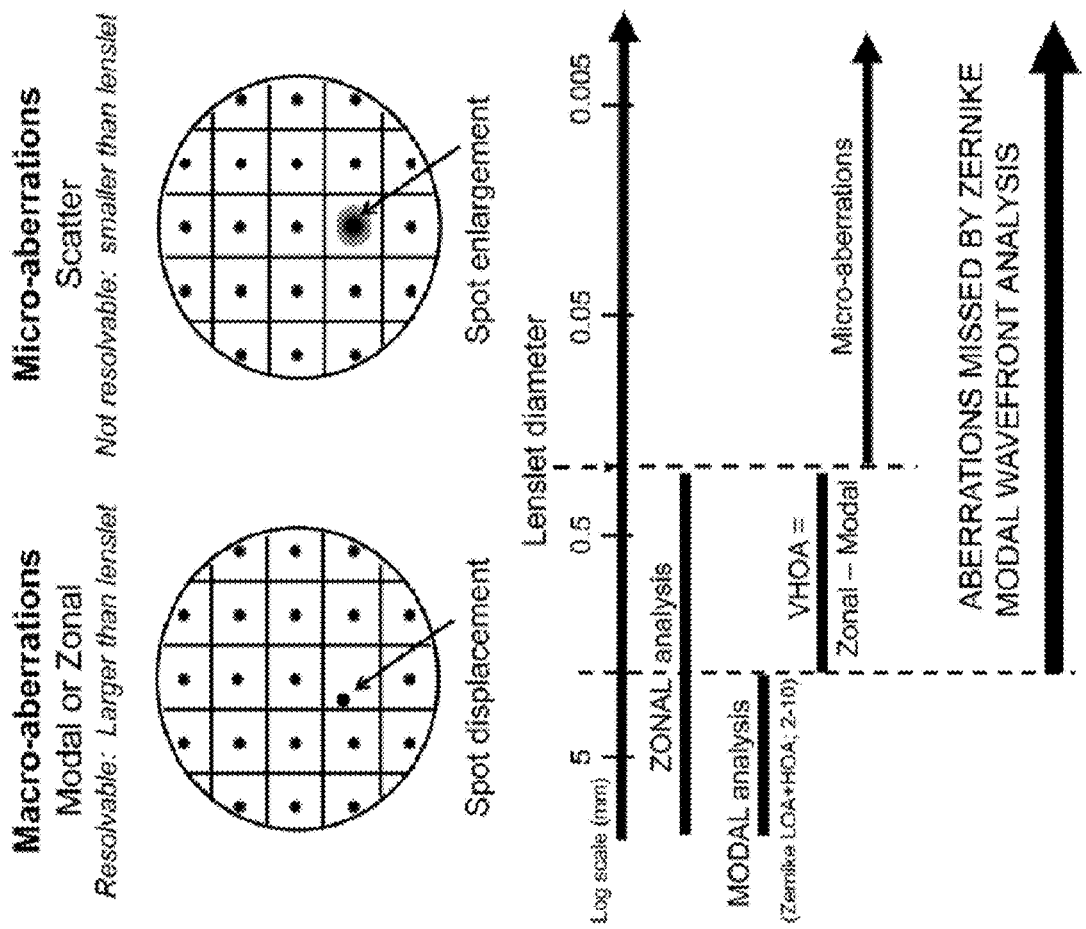
FIG. 3 illustrates the concepts of macro-aberrations and micro-aberrations in spots appearing on a Shack-Hartmann wavefront sensor due to tear breakup for an eye.

FIG. 3 illustrates the concepts of macro-aberrations and micro-aberrations in spots appearing on a Shack-Hartmann wavefront sensor due to tear breakup for an eye, as described in Himebaugh et al., cited above.

In particular, raw Shack-Hartmann data are shown in the top part of this figure. The left panel shows spot displacement (left arrow) as the basis of determination of macro-aberrations, while the right hand panel shows spot enlargement (right arrow) caused by micro-aberrations. The bottom half of this figure shows a size scale with courser aberrations on the left and finer aberrations on the right, quantified in mm in the pupil plane. The lines show the size range of macro-aberrations determined with either modal or zonal analysis, or from the difference between zonal and modal fitted wavefronts. Aberrations on a scale smaller than the lenslet diameter are indicated as micro-aberrations. The range of spatial scale missed by classic Zernike analysis is indicated by the thick black arrow.

The nature of the tear film break up will affect the appearance of the spots. An intact tear film is made of three layers. The first layer is an outer lipid layer that retards evaporation of the second aqueous layer and then a third mucous layer that enables the aqueous layer to adhere to the hydrophobic cornea. The cornea itself is rough in comparison to the mucous layer. So the nature of the spots on the Shack-Hartmann sensor is altered according to which layers of the tear film are disrupted and this information can help identify particular tear film pathologies. Inadequate production of the lipids, aqueous or mucous will lead to different spot patterns on the sensor. Excessive production of aqueous also leads to distinctive spot patterns of a wavelike nature that flow. Excessive aqueous production is often caused by eye discomfort due to a variety causes. In comparison to the other layers, the mucous layer is slower to re-fill once it has been disturbed. The slow fill-in appears in time series data as regions where disturbed spots appear very quickly after a blink because of the water repelling nature of the bare cornea. Lipid layer breakup occurs at a slow rate.

The appearance of an individual Shack-Hartmann spot is influenced by several factors besides the tear film. The factors include the spectral bandwidth of the probe beam, the projected spot size of the probe beam on the retina, scatter in the ocular media of the eye, the limiting apertures inside the instrument, and the width of each lenslet in the lenslet array in the wavefront sensor. Narrow spectral bandwidths, like a laser, cause speckle patterns in the individual spots that cause spot breakup. A wide band source like a superluminescent laser diode (SLD) produces very little speckle so the use of those is advantageous in this application. An increase of the size of the projected probe beam spot on the retina causes an increased spot size on the sensor. Larger limiting apertures in the instrument optical system allow more light scattered from inside the eye to reach the sensor, increasing the spot size. Obviously smaller lenslets correspond to smaller sample areas on the cornea which help map tear film features but in addition speckle patterns from bandwidth considerations are also affected.

Neal et al disclosed a method in which the size of an aperture was increased during a measurement sequence to increase the amount of scattered light that reaches a wavefront sensor for the purpose of quantifying cataracts in the eye. Scatter from a disturbed mucous layer would similarly cause increased scatter and would show up on a Shack-Hartman wavefront sensor producing larger spots. A similar effect would be seen on a camera which forms a regular image of the topography spots, with change increases in the telecentric stop diameter increasing the spot size due to increases in scatter light capture.

Figure 4:
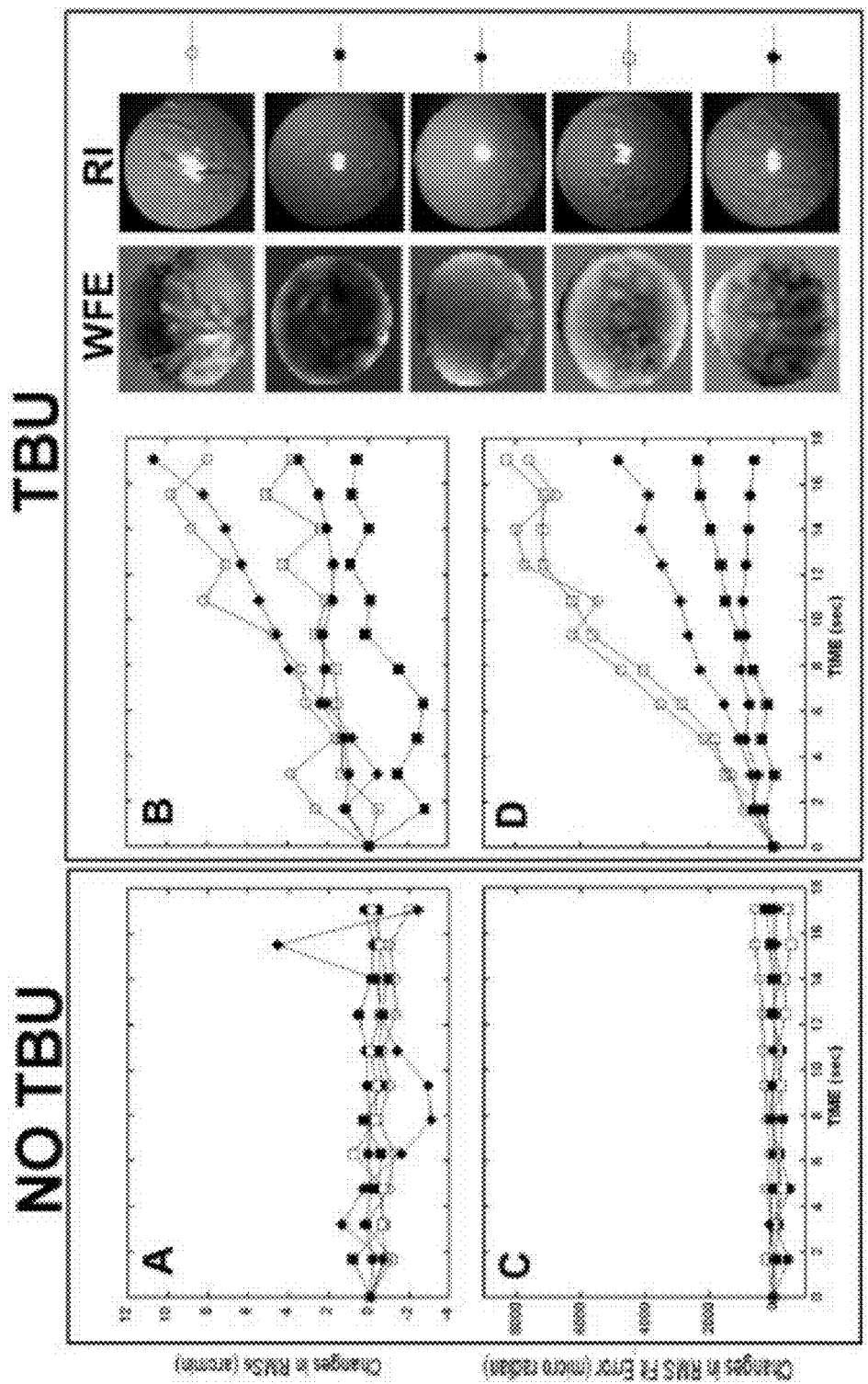
FIG. 4 illustrates changes in a root-mean-square (RMS) optical quality metric as a function of time since the last blink for some example subjects who experienced no tear film breakup, and some other example subjects who did experience tear film breakup.

FIG. 4 illustrates changes in a root-mean-square (RMS) optical quality metric as a function of time since the last blink for some example subjects who experienced no tear film breakup, and some other example subjects who did experience tear film breakup, as discussed in Liu et al. Here the horizontal axis represents the time since the last blink, and the vertical axis represents the gradient RMS fit error (GFE) as a metric for visual acuity. The GFE represents a residual error after achieving a best fit of the wavefront data to a Zernike polynomial gradient of a particular order, for example a $4^{th}$ order Zernike polynomial. WFFE can be calculated from the gradient fit errors ($\sigma_x$, $\sigma_y$) as:

$$WFFE = \frac{d}{m}\sqrt{\sigma_x^2 + \sigma_y^2} \tag{1}$$

Figure 5:
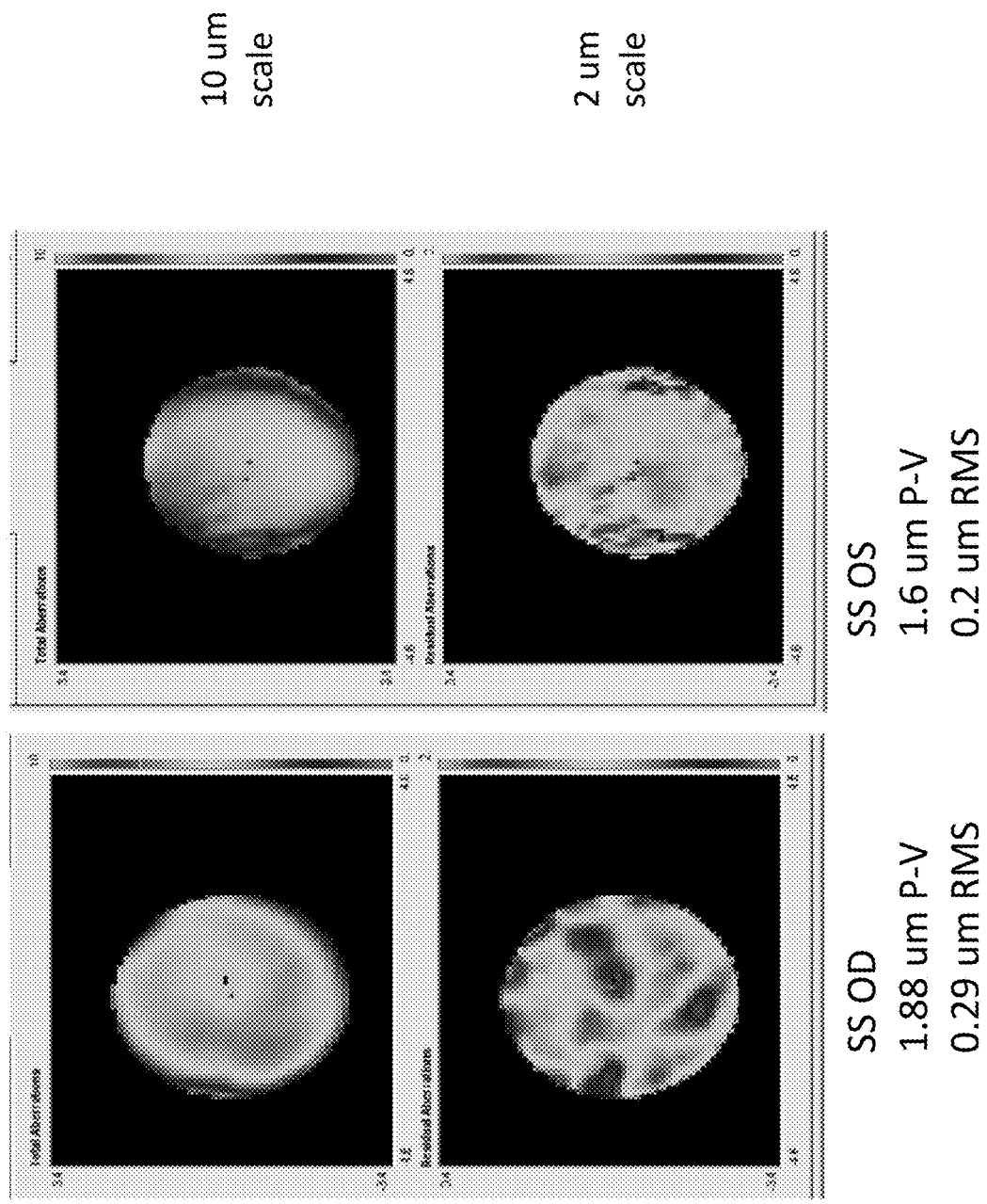
FIG. 5 shows total aberrations and remaining aberrations after a best fit to a Zernike polynomial, illustrating how Zonal-Modal RMS may indicate some eye conditions.

FIG. 5 shows an example eye measurement with total aberrations (top) and remaining aberrations (bottom) after a best fit to a Zernike polynomial, illustrating how Zonal-Modal RMS may indicate some eye conditions, for example corneal scarring from Herpes virus. In particular, FIG. 5 illustrates that there can be significant aberration that is not well represented by Zernike polynomials. The difference allows a direct identification of Zernike fit errors. The Zonal-Modal RMS value reveals the quality of the Zernike fit in wavefront units. The wavefront Zonal-Modal irregularity may be calculated from:

$$w_{Z-M,fit}^2 = \frac{1}{N}\sum_k \left(w_k - \sum_{m=2}^{M} C_m P_m(x_k, y_k)\right)^2 \tag{2}$$

The difference between the Zonal-Modal approach and the WFFE fit error is that one is derived from the gradient fit process and the other from a difference of the reconstructed surfaces. They have been shown to correlate very well to each other. For some surfaces that have sharp steps (such as when a tear film breaks up) the Z-M irregularity may be more sensitive than the WFFE.

Figure 6C:
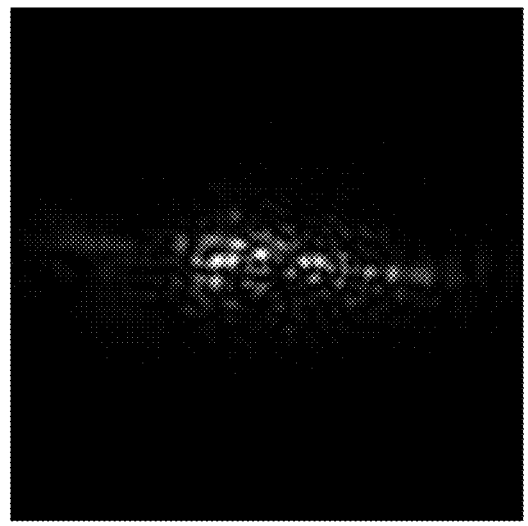
FIGS. 6A, 6B, and 6C illustrate changes in the point spread function of wavefront data for an example eye as a function of time, due to tear film breakup or irregularity.
Figure 6B:
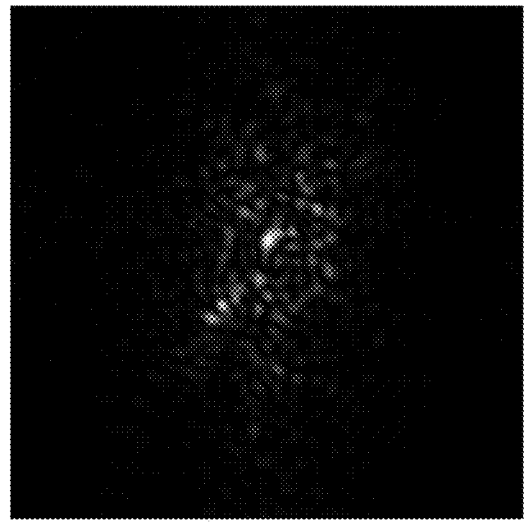
Figure 6A:
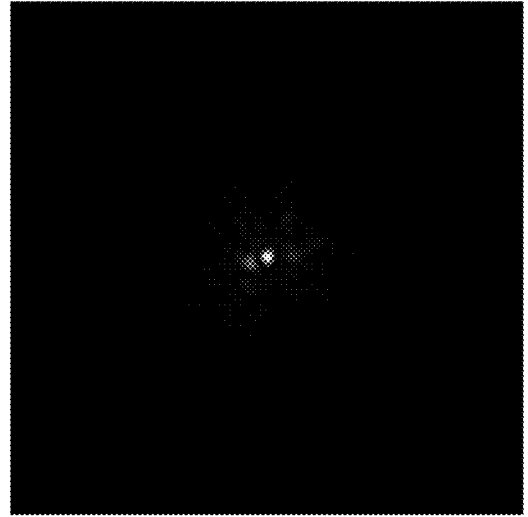

FIGS. 6A, 6B, and 6C illustrate changes in the point spread function of wavefront data for an example eye, as a function of time, due to tear film breakup. In FIGS. 6A, 6B and 6C, the diameter of a "dot" is about half the angular size of the horizontal crossbar of the "e" on the bottom line of a standard eye chart. Here, FIG. 6A is produced from wavefront data taken about 0.61 seconds after a blink, FIG. 6B is produced from wavefront data taken about 12.6 seconds after the blink, and FIG. 6C is produced from wavefront data taken about 31.3 seconds after the blink.

The point spread function (PSF) describes the image quality of a system. PSF and "far-field" intensity distribution are equivalent. The near field is determined by the wavefront sensor (WFS) intensity and phase measurements:

$$U(x, y) = \sqrt{I(x, y)}\, e^{\frac{2\pi i}{\lambda}\phi(x,y)} \tag{3}$$

The far-field may be determined from the Fourier transform of the near field:

$$U(u, v) = \int_{-\frac{a}{2}}^{\frac{a}{2}}\int_{-\frac{b}{2}}^{\frac{b}{2}} U(x, y)\exp\left[-\frac{2\pi i}{\lambda}(xu + yv)\right] dxdy \tag{4}$$

PSF can be calculated from the far-field:

$$P(f) = |F\{U(u,v)\}|^2 \tag{5}$$

The 2nd moment of the PSF is a measure of how much (on average) the point-spread-function has spread. It describes the angular divergence, and the angular divergence can be used to relate to resolution, Snellen acuity, LogMAR, etc, through standard methods. More information about this may be found in Michael Keating, "*Geometric, Physical and Visual Optics*," ELSEVIER PUBLISHING COMPANY.

Figure 7:
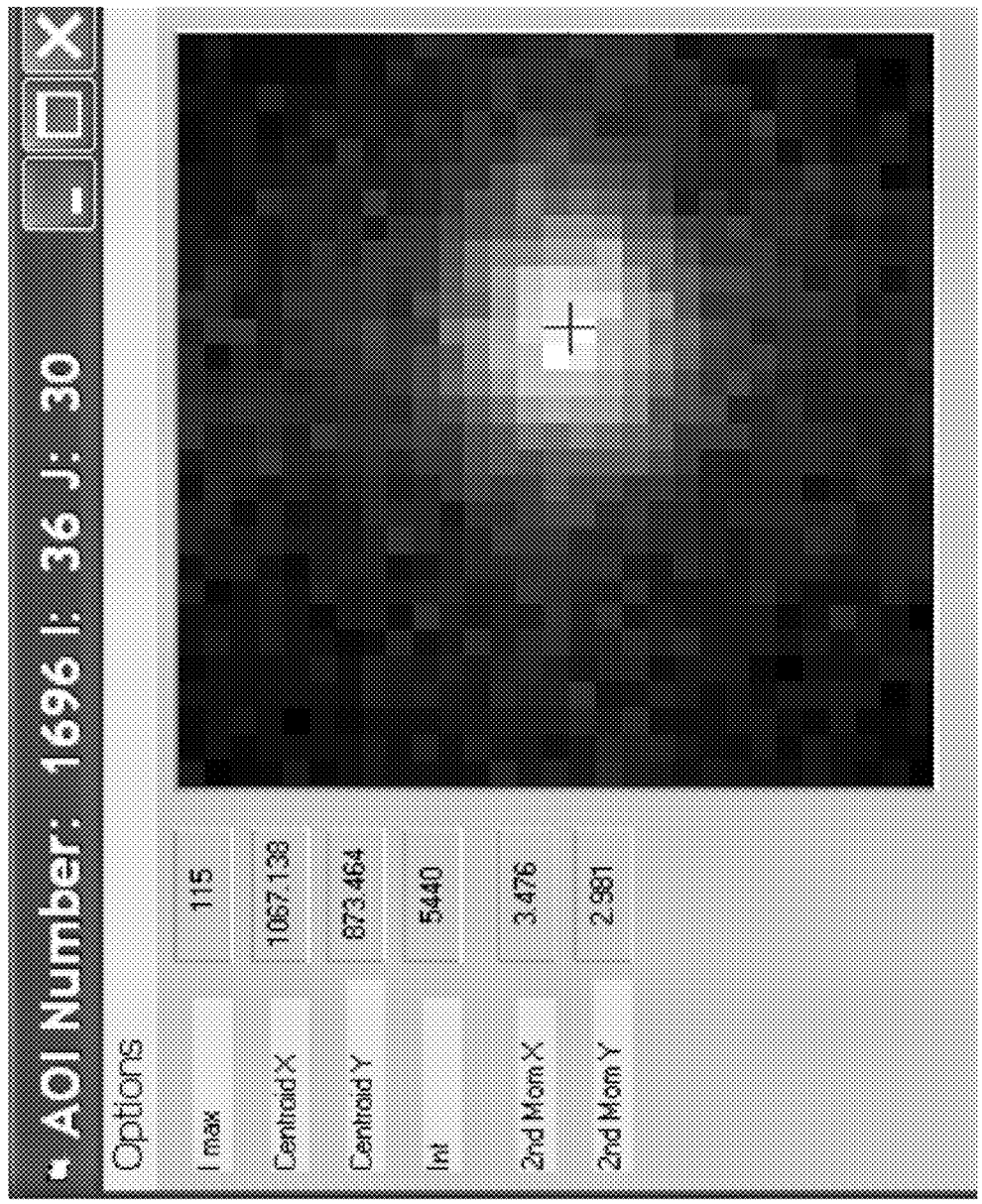
FIG. 7 illustrates an example of one spot at a detector produced from a wavefront of an example eye by one lenslet of a Shack-Hartmann wavefront sensor for illustrating some measurements of micro-aberrations in the wavefront which may be employed to quantify the tear film breakup.

FIG. 7 illustrates an example of one spot at a detector produced from a wavefront of an example eye by one lenslet of a Shack-Hartmann wavefront sensor for illustrating some measurements of micro-aberrations in the wavefront which may be employed to quantify the tear film breakup. Changes in the sizes of the spots produced on the detector as a function of time may be employed to produce a metric for evaluating tear film breakup.

One measure of the size of the spot is its equivalent width, which is the width of an equivalent "cylinder" for the spot having the same "height" and volume, where the "height" represents the intensity of the light spot.

Another measure of the size of the spot is the second moment, which can be calculated as:

$$\sigma_x^2 = \iint I(x,y)(x-\bar{x})^2 dxdy / \iint I(x,y) dxdy \tag{6}$$

The values of the second moments of the spot sizes of a wavefront image may be added or subtracted, are independent of distribution, and equal to ½ of the equivalent width.

Another measure of the size of the spot is the far field divergence angle per wavefront sensor lenslet:

$$\theta_x = M\sigma_x/f \tag{7}$$

where $\sigma_x$ is the $2^{nd}$ moment of the distribution from an individual lenslet. This may be averaged over the pupil as:

$$\theta_{RMS} = M\bar{\sigma}/f \tag{8}$$

Figure 8:
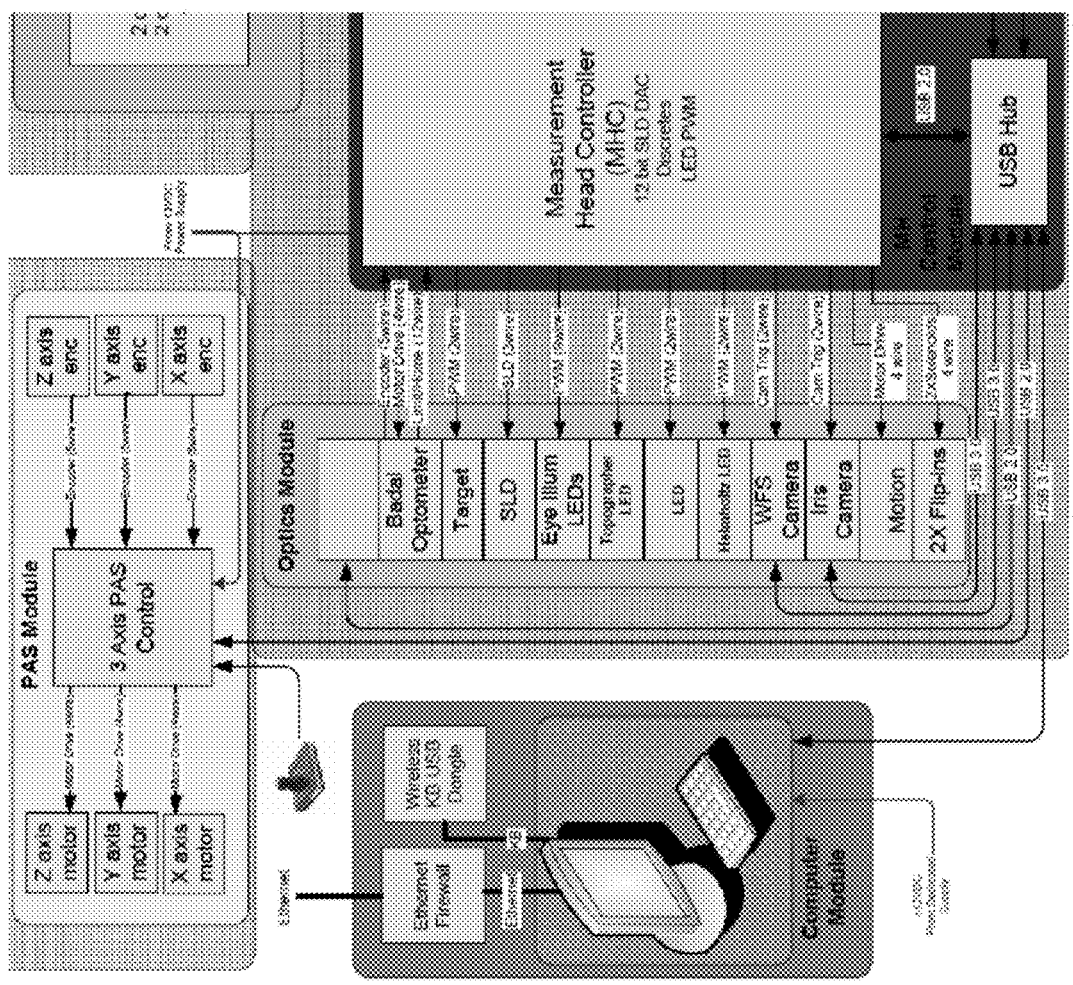
FIG. 8 illustrates an example embodiment of an optical measurement instrument which includes a wavefront aberrometer and a corneal topographer which may be employed to make measurements for quantifying the tear film breakup of an eye.

FIG. 8 illustrates an example embodiment of an optical measurement instrument which includes a wavefront aberrometer and a corneal topographer which may be employed to make measurements for quantifying the tear film breakup of an eye. Here, the wavefront aberrometer may be a Shack-Hartmann wavefront sensor having a high density lenslet array (f=2.78 mm; d=0.1092 mm) and a high resolution camera (detector) comprising, for example, 1920× 1080 3.69-um pixels, updated at a frame rate, for example, of 26 Hz, operating in a synch mode with a short shutter time. The large pixel-count, small pixel-size camera results in a fairly large number of pixels assigned to each lenslet. This allows for a measure of the scattering within each lenslet (objectively determined by the $2^{nd}$ moment method). In a preferred embodiment, the corneal topographer may comprise an Full Gradient Corneal Topographer (FGCT) cone with central pattern projection (often called a Helmholtz Source, HHS) and a high resolution camera (detector) comprising, for example, 1920×1080 3.69-um pixels. Other embodiments would include a placido, ring topographer, grid-projection topographer or other methods where a spatially distributed measure of the local image distortion can be combined with local variations in the topographic surface.

The optical measurement instrument includes a processor which may process the wavefront aberrometry data and the corneal topography data to produce combined tear film breakup data as a function of time, operative as a metric for evaluating a level of tear film breakup of the eye as a function of time.

The optical measurement instrument also includes a controller to synchronize operations of the cameras and light sources of the wavefront aberrometer and the corneal topographer. Beneficially, the controller may control the wavefront aberrometer and the corneal topographer such that each of a plurality of sets of wavefront aberrometry data is obtained nearly simultaneously with a corresponding set of corneal topography data. In some embodiments, as illustrated below with respect to FIG. 10, the controller may control the wavefront aberrometer and the corneal topographer so as to obtain set of wavefront aberrometry data and one set of corneal topography data in each of a plurality of consecutive time frames. In some embodiments, the time frame may be about 30 milliseconds long. In other embodiments, high speed cameras may be employed to obtain information about the dynamics of the tear film itself.

Figure 9:
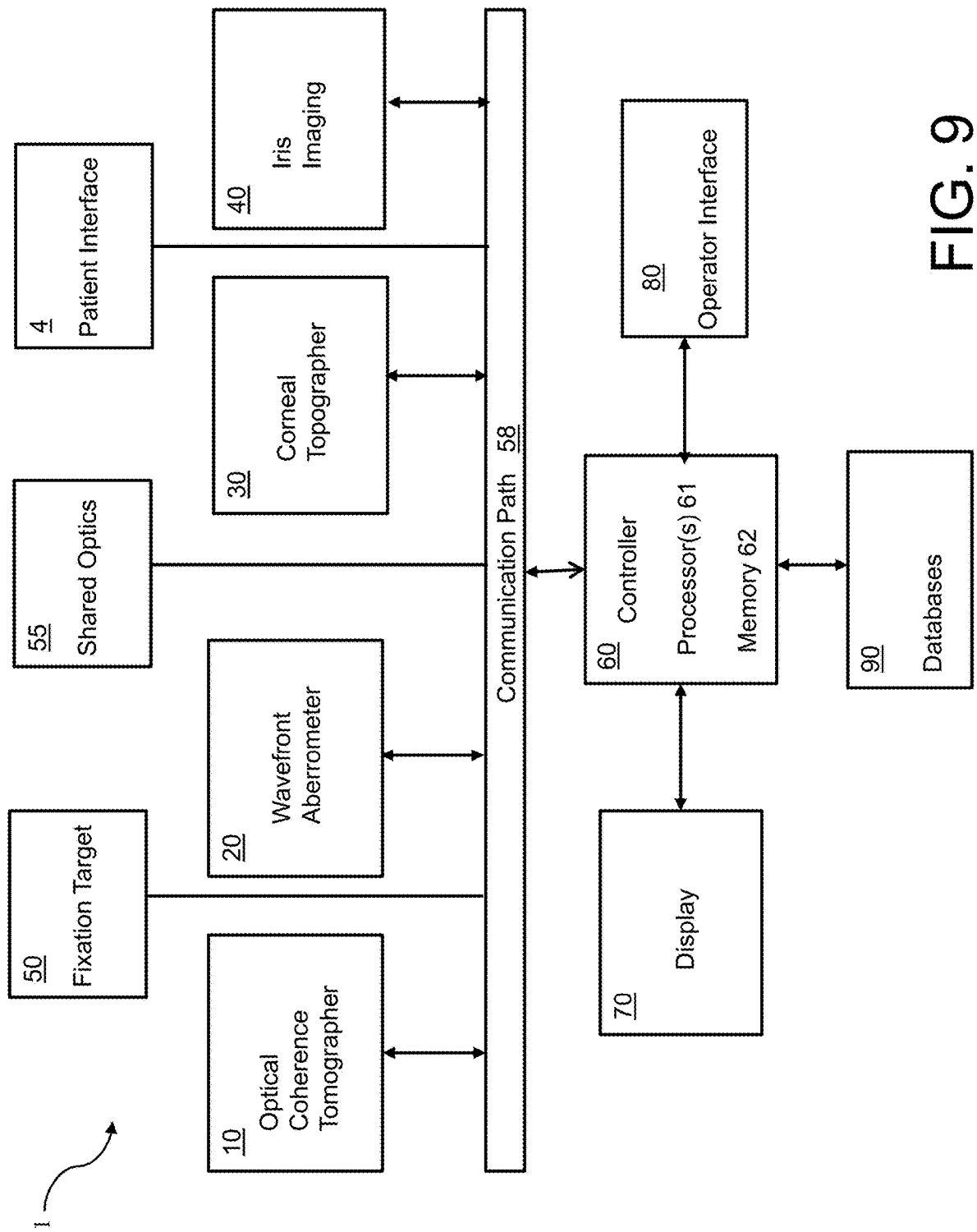
FIG. 9 is a functional block diagram of an example embodiment of an optical measurement instrument which may be employed to make measurements for quantifying the tear film breakup of an eye.

FIG. 9 is a functional block diagram of an example embodiment of an optical measurement instrument which may be employed to make measurements for quantifying the tear film breakup of an eye. Further details of an example of such an instrument are provided in U.S. patent application Ser. No. 14/969,264, "OPTICAL IMAGING AND MEASUREMENT SYSTEMS AND METHODS FOR CATARACT SURGERY AND TREATMENT PLANNING," filed on 15 Dec. 2015, the entirety of which is incorporated herein by reference. In other embodiments, one or more of the subsystems or elements of this optical measurement instrument may be omitted (e.g., the optical coherence tomographer (OCT)). Further details of optical measurement instruments which may be suitable for practicing one or more aspects of the present invention may be found in: U.S. Pat. No. 7,988,293, "METHOD OF QUALIFYING LIGHT SPOTS FOR OPTICAL MEASUREMENTS AND MEASUREMENT INSTRUMENT EMPLOYING METHOD OF QUALIFYING LIGHT SPOTS," issued on 2 Aug. 2011; U.S. patent application Ser. No. 14/789,943, "OPTICAL MEASUREMENT SYSTEM AND METHOD INCLUDING BLINK RATE MONITOR AND/OR TEAR FILM BREAKUP DETECTOR," filed on 1 Jul. 2015; U.S. patent application Ser. No. 14/791,175, "OPTICAL MEASUREMENT SYSTEM AND METHOD WITH TARGET BRIGHTNESS LEVEL ADJUSTMENT," filed on 2 Jul. 2015; U.S. patent application Ser. No. 13/341,385, "TREATMENT PLANNING METHOD AND SYSTEM FOR CONTROLLING LASER REFRACTIVE SURGERY," filed on 30 Dec. 2011; U.S. patent application Ser. No. 14/949,757, "METHOD AND SYSTEM FOR EYE MEASUREMENTS AND CATARACT SURGERY PLANNING USING VECTOR FUNCTION DERIVED FROM PRIOR SURGERIES," filed on 23 Nov. 2013; U.S. patent application Ser. No. 14/949,783, "METHOD AND SYSTEM FOR EYE MEASUREMENTS AND CATARACT SURGERY PLANNING USING VECTOR FUNCTION DERIVED FROM PRIOR SURGERIES," filed on 23 Nov. 2013; and U.S. patent application Ser. No. 14/949,797, "METHOD AND SYSTEM FOR EYE MEASUREMENTS AND CATARACT SURGERY PLANNING USING VECTOR FUNCTION DERIVED FROM PRIOR SURGERIES," filed on 23 Nov. 2013, all of which are incorporated herein by reference.

Alternatively, there may be information that can be obtained by OCT measurements that could be useful in interpreting tear film measurements. The scheme described in FIG. 10 can be extended to include other measurements, including an OCT measurement. This would allow for a 3D measure of the tear film thickness. While the OCT resolution is usually lower than that of a topographer or aberrometer, the accuracy of the measurement can be improved by using the simultaneous corneal topography measurements which provide very accurate measurements of the anterior surface.

Figure 10:
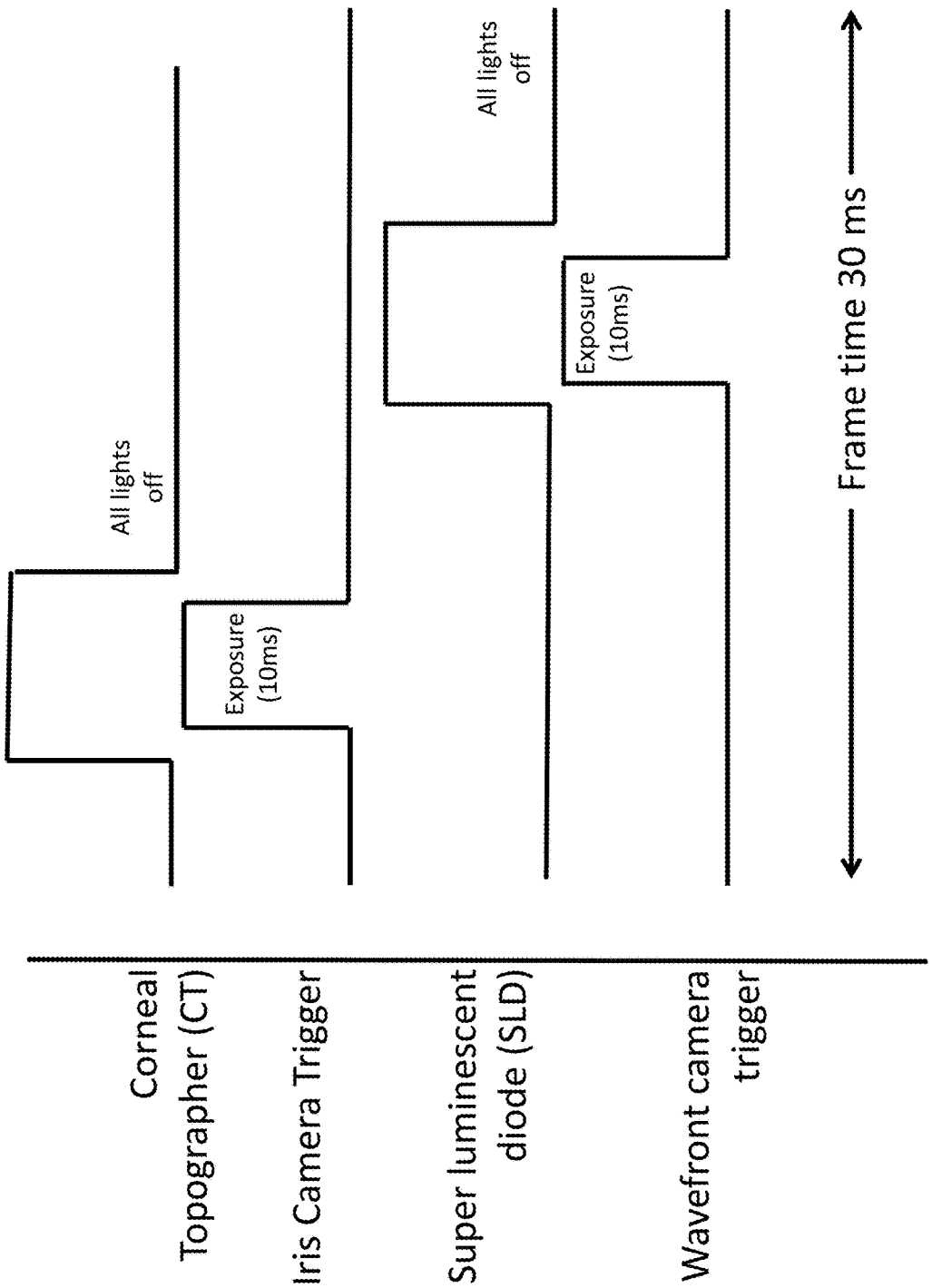
FIG. 10 illustrates an example of timing for camera multiplexing for making a near-simultaneous series of corneal topography and wavefront aberrometry measurements of an eye.

FIG. 10 illustrates an example of timing for camera multiplexing for making a near-simultaneous series of corneal topography and wavefront aberrometry measurements of an eye, as described above.

FIGS. 11 through 26 were produced by processing wavefront and corneal topography data collected from a subject over a timeframe of forty seconds. The subject was instructed to "hold your eye open as long as possible between blinks" and the system provided aural countdown for remaining time as a guide to the subject. Many such sequences were recorded for a variety of subjects, but one sequence was selected as representative for data analysis.

Another type of acquisition sequence would consist of asking the subject to "blink normally," In this scenario, information regarding normal blink rate, blink completeness, and other parameters could be acquired simultaneous with the tear film metric. This step may also be combined with measuring the subject refraction and corneal topography.

Figure 11A:
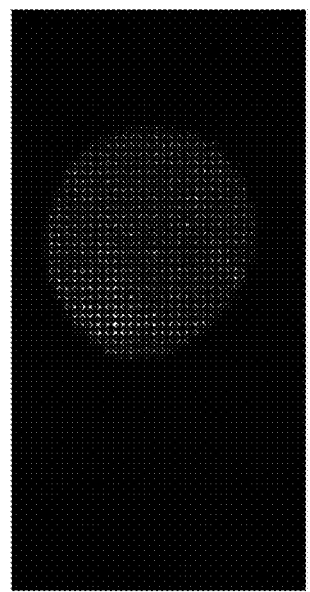
FIGS. 11A and 11B illustrate corneal topography data and wavefront aberrometry data, respectively, for an example eye measured at a first time shortly after a blink.
Figure 11B:
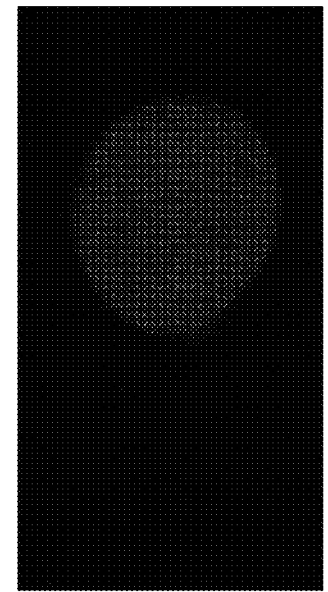
Figure 11C:
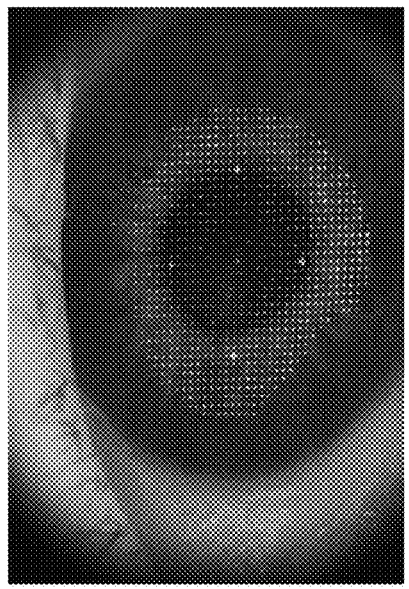
FIGS. 11C and 11D illustrate corneal topography data and wavefront aberrometry data, respectively, for the same eye measured several seconds later after the blink.
Figure 11D:
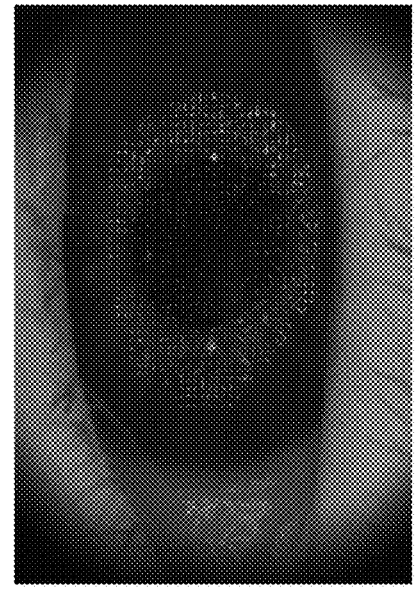

FIGS. 11A and 11B illustrate corneal topography data and wavefront aberrometry data, respectively, for an example eye measured at a first time shortly after a blink, and FIGS. 11C and 11D illustrate corneal topography data and wavefront aberrometry data, respectively, for the same eye measured several seconds later after the blink.

Figure 12:
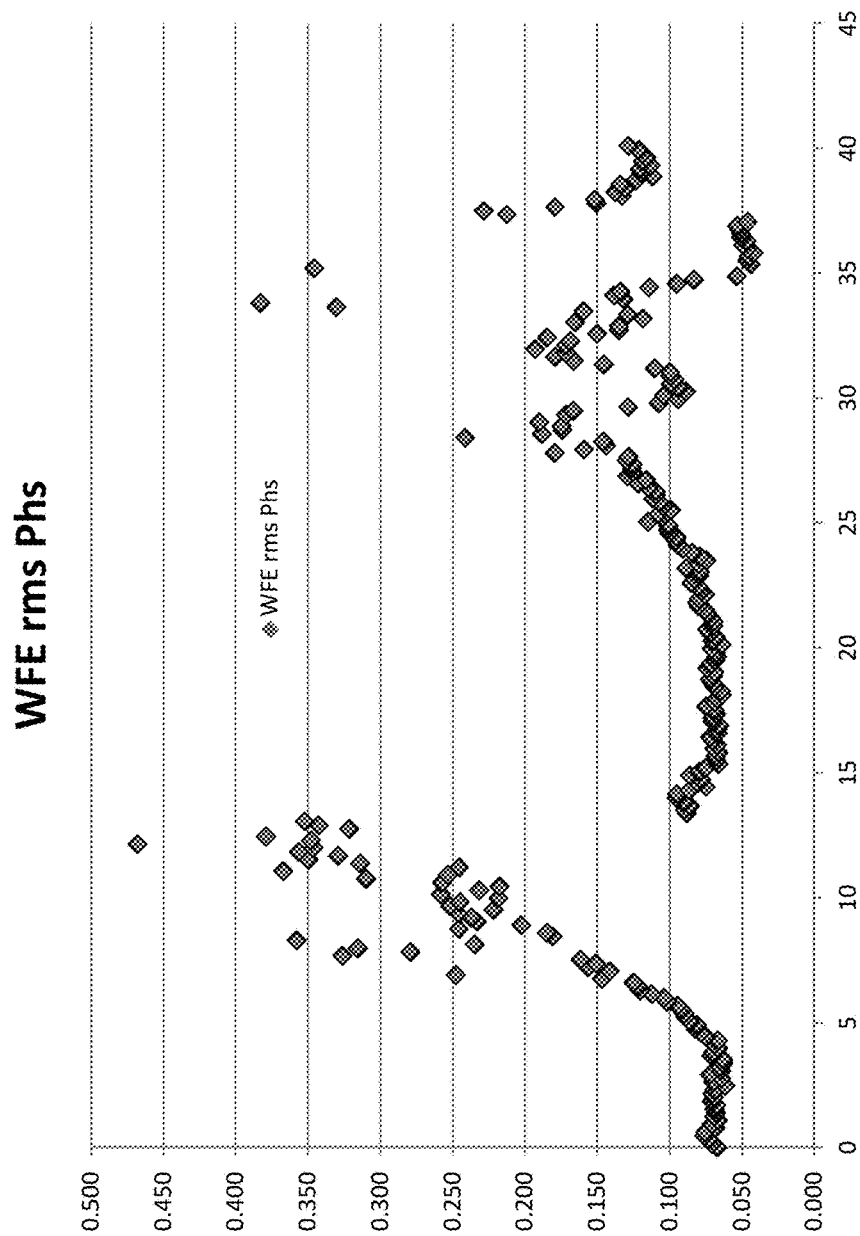
FIG. 12 plots an example of RMS wavefront fit error for an example eye as a function of time from an initial blink.

FIG. 12 plots an example of RMS wavefront fit error for the example eye as a function of time from an initial blink. Here it can be observed that RMS wavefront fit error is sensitive to tear film variation.

Figure 13:
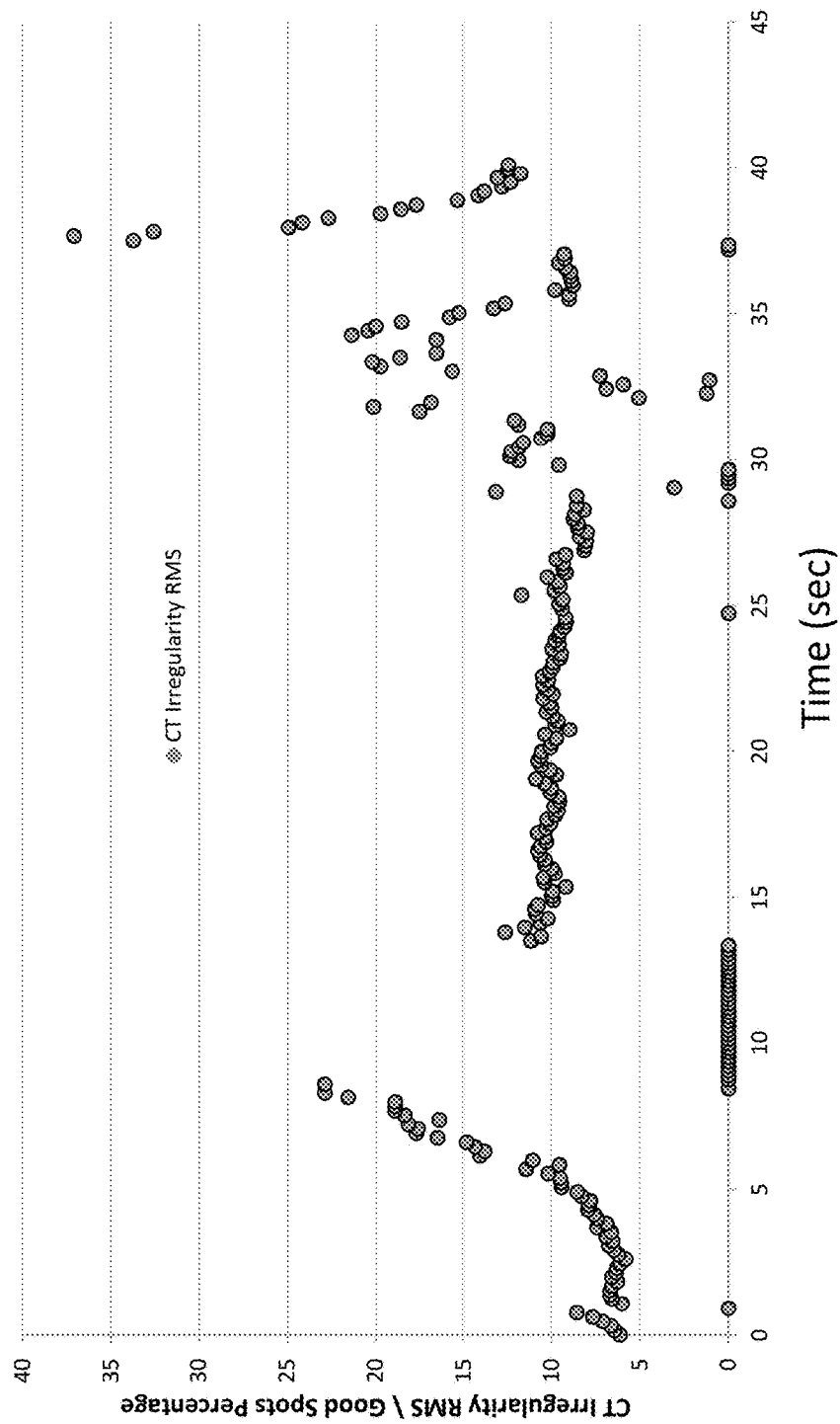
FIG. 13 plots an example of RMS corneal topography irregularity for an example eye as a function of time from an initial blink.

FIG. 13 plots an example of RMS corneal topography irregularity for an example eye as a function of time from an initial blink. Here it can be observed that RMS corneal topography irregularity is sensitive to tear film variation.

Figure 14:
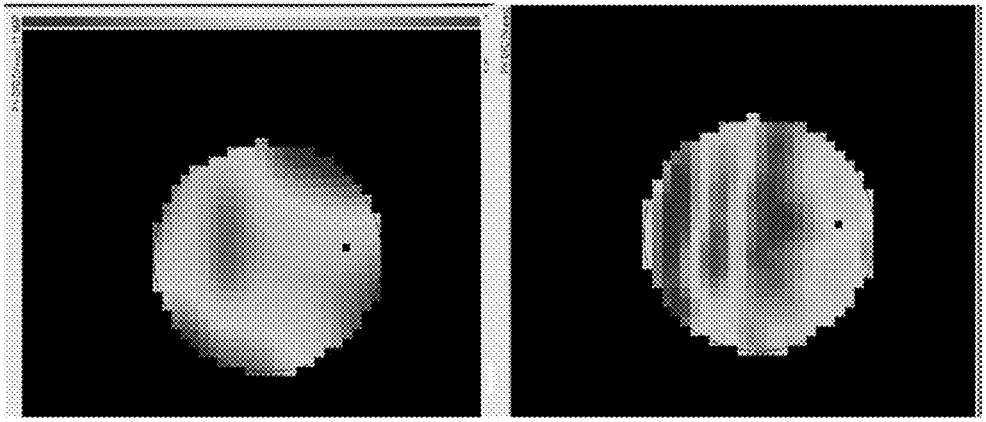
FIG. 14 illustrates examples of low and high order wavefront aberrations, and very high order wavefront aberrations, at different points in time with respect to a previous blink for an example eye.
Figure 14:
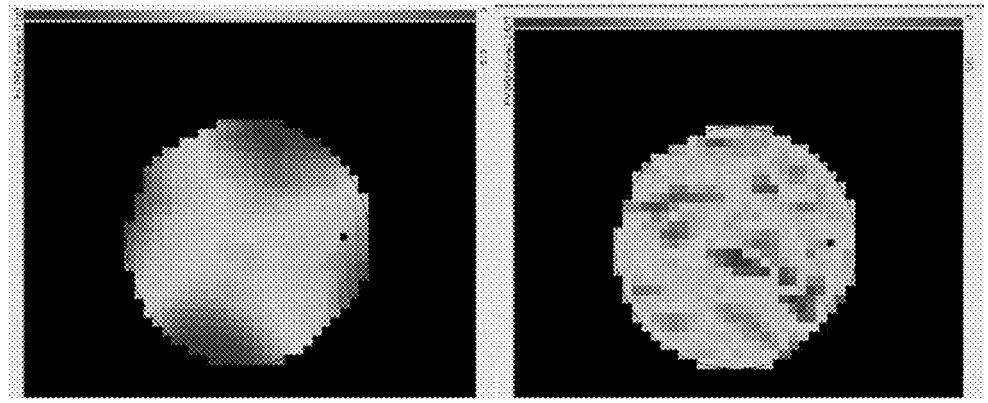
Figure 14:
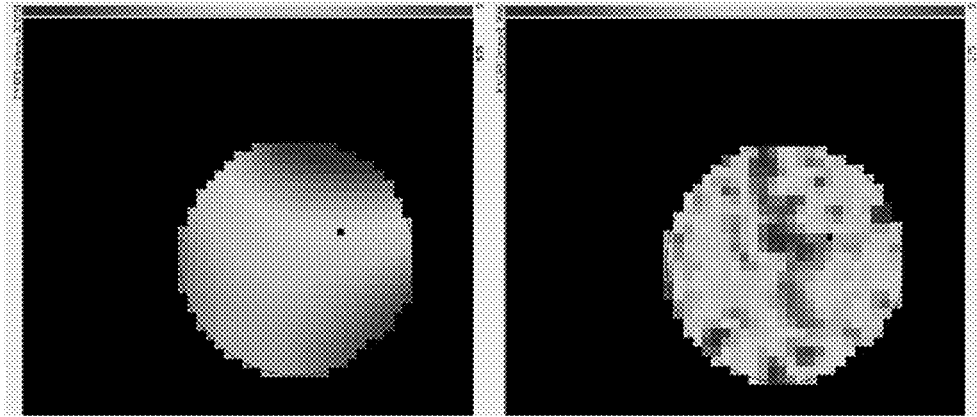

FIG. 14 illustrates examples of low and high order wavefront aberrations, and very high order wavefront aberrations, at different points in time with respect to a previous blink for an example eye. The three images at the top of FIG. 14 represent low and high order aberrations, and the three images at the bottom of FIG. 14 represent very high order aberrations. The differences in the grey scales in the bottom images represent waves of tears in the tear film.

Figure 15:
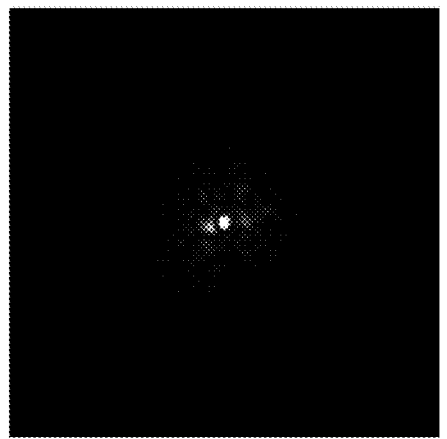
FIG. 15 illustrates examples of a full pupil point spread function for an example eye at different points in time with respect to a previous blink.
Figure 15:
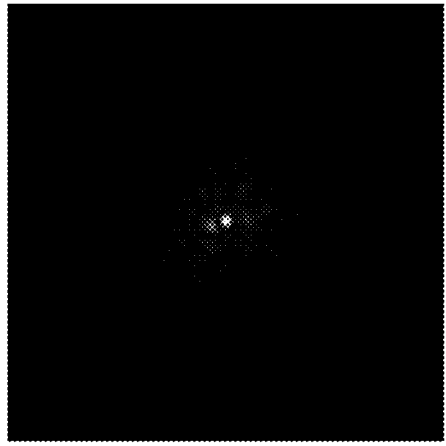
Figure 15:
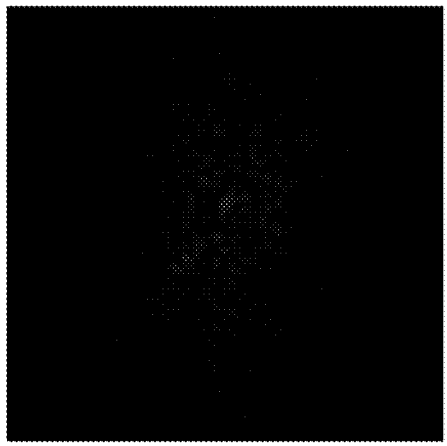
Figure 15:
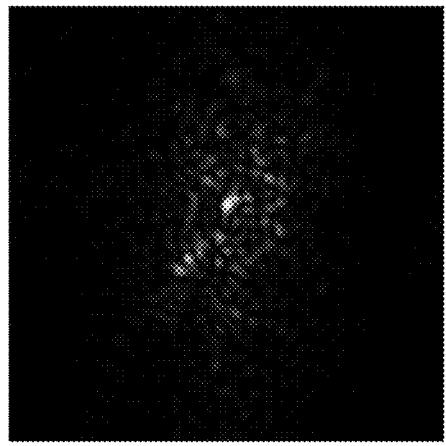
Figure 15:
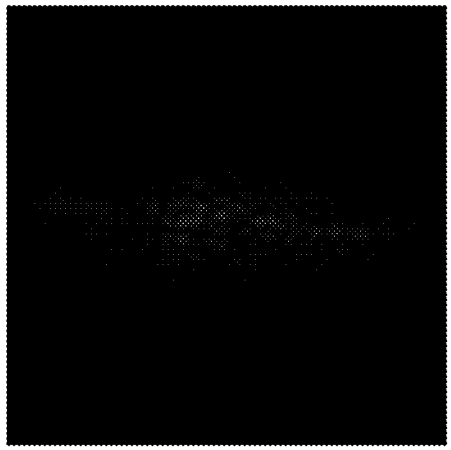
Figure 15:
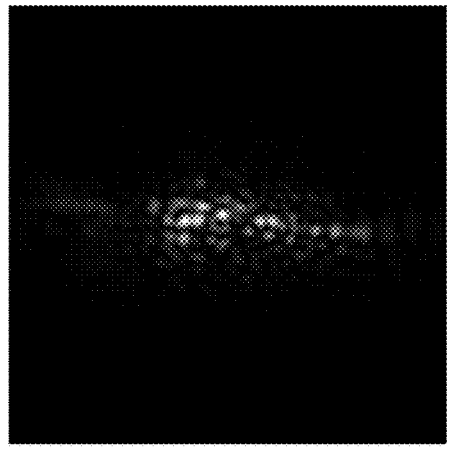

FIG. 15 illustrates examples of a full pupil point spread function for an example eye at different points in time with respect to a previous blink. The upper three images in FIG.

15 represent the actual point spread functions, while the bottom three images in FIG. 15 represent the same data, readjusted or normalized such that all three images have the same peak brightness as each other.

Beneficially, a processor may evaluate the characteristics of images such as those shown in FIGS. 14 and 15 to distinguish between different mechanisms of tear film breakup. Right after the blink (FIG. 6A) the point-spread-function is well confined, with most energy in a single central peak. This corresponds to the wavefront for FIG. 14. At 12.6 seconds (corresponding to FIG. 14B), the point-spread-function is quite distorted. The individual focal spots of the Shack-Hartmann sensor are quite distorted (FIG. 18) and the corneal topography (FIG. 22) shows a highly distorted image as well. This is due to the highly irregular wavefront of FIG. 14B. The combination of these factors indicates that the tear film has broken up in regions. Thus the correlation of factors: wavefront irregularity, average $2^{nd}$ moment spot size, number of bad CT spots, fraction of bad CT spots, and point spread function angular divergence point until tear film break up. This can be determined purely through objective methods.

At 31.3 seconds after the initial blink, there is a different situation, however. Comparing FIGS. 14C, 15C, and 22C, it is apparent that the individual focal spots are not overly distorted. The topography image is fairly regular and the individual regions have little distortion. Yet the point-spread-function shows a large divergence in the vertical direction. Examination of the individual SHWFS spots shows that these are relatively un-distorted as well. In this case the point-spread-function is caused by the vertical "waves" in the wavefront as measured by both the corneal and WF irregularity (zonal-modal) maps. This is a case where the tear film is NOT broken up, but is irregular. This is due to the eye responding to the prolonged period between blinks by releasing a large quantity of tear liquid. Prior to a blink the tear liquid surface is irregular. Thus the correlation of metrics allows for the discrimination between optical effects caused by too little tears (tear film break up) and too much tear liquid (pooling).

Since the treatment for various tear film conditions is different depending upon the exact nature of the tear film condition, this object means for discrimination between conditions can be an important part of the diagnosis. For too-little tear film, the treatment might include eye-drops, artificial tears, or even plugging the tear-duct drains. If the problem is too much tear production, then plugging the ducts would exacerbate the condition. Hence it is important to be able to distinguish between tear film conditions.

Figure 16:
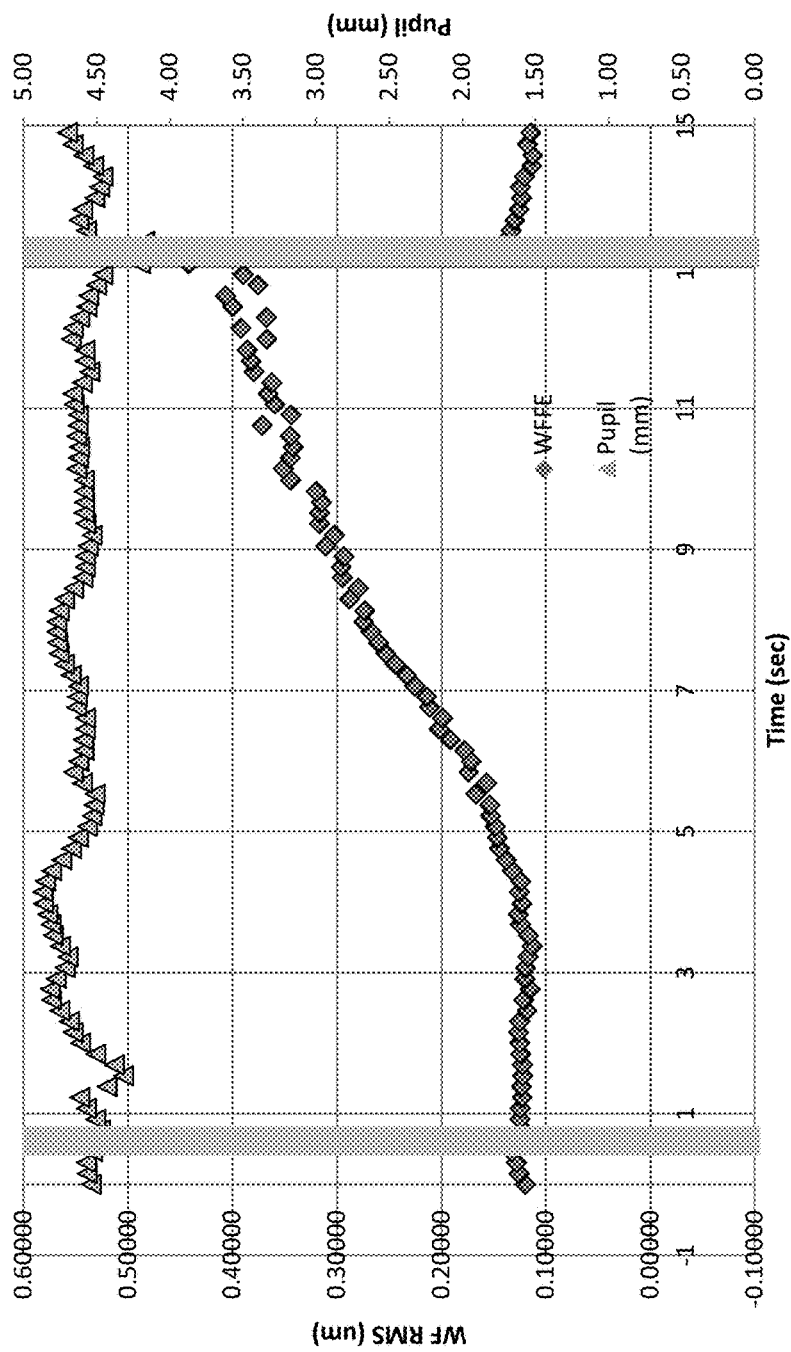
FIG. 16 illustrates an example of wavefront fit error to a $4^{th}$ order Zernike polynomial for an eye as a function of time. The pupil size is also shown for reference.

FIG. 16 illustrates an example of wavefront fit error to a $4^{th}$ order Zernike polynomial for an eye as a function of time. Here, each of the two thick vertical bars represents a time interval during which a blink occurred.

Figure 17:
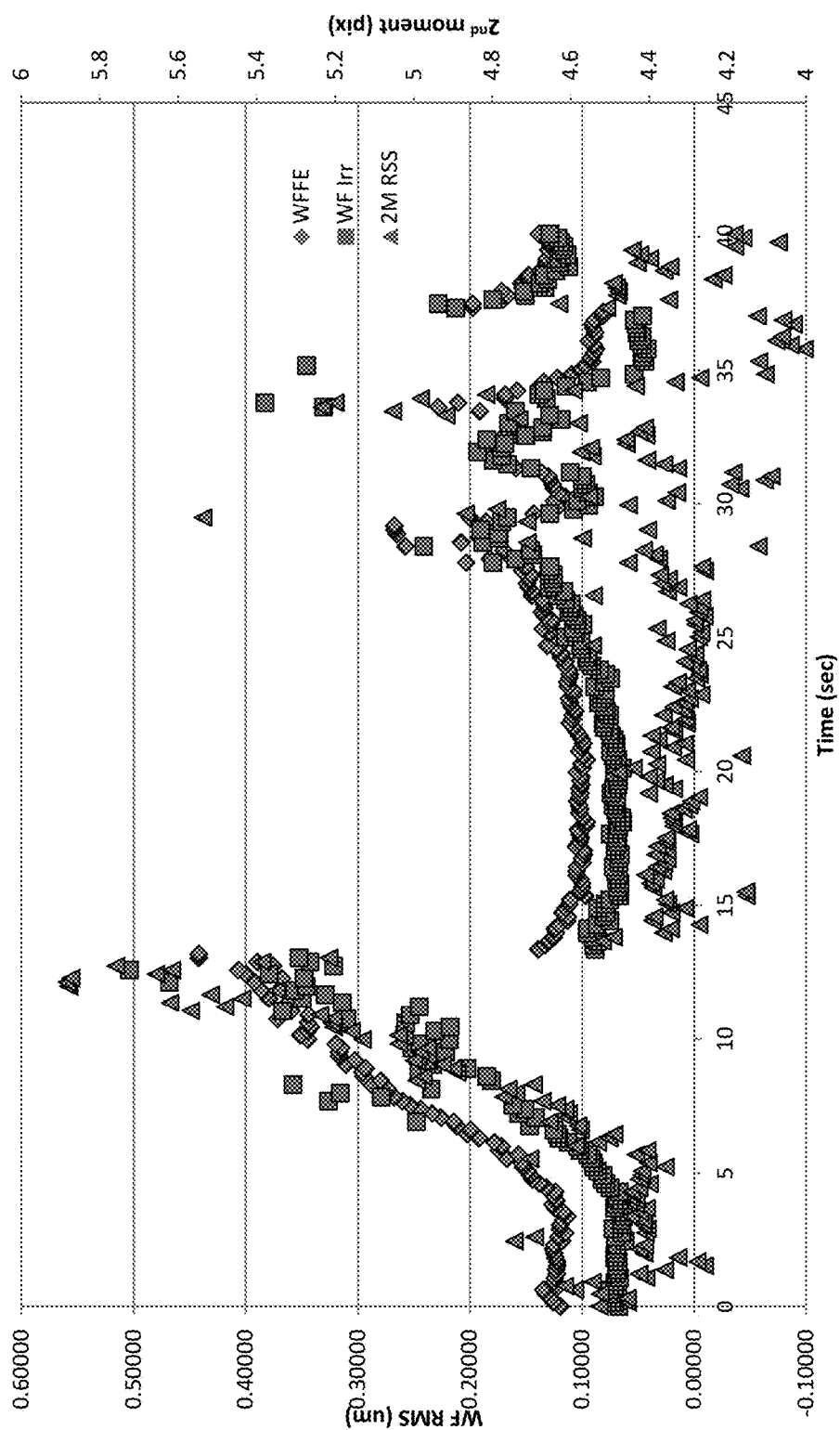
FIG. 17 illustrates how the $2^{nd}$ moment RSS spot size as a function of time correlates with wavefront fit error and wavefront irregularity for an example eye.

FIG. 17 illustrates how the $2^{nd}$ moment RSS spot size as a function of time correlates with wavefront fit error and wavefront irregularity for an example eye.

Figure 18:
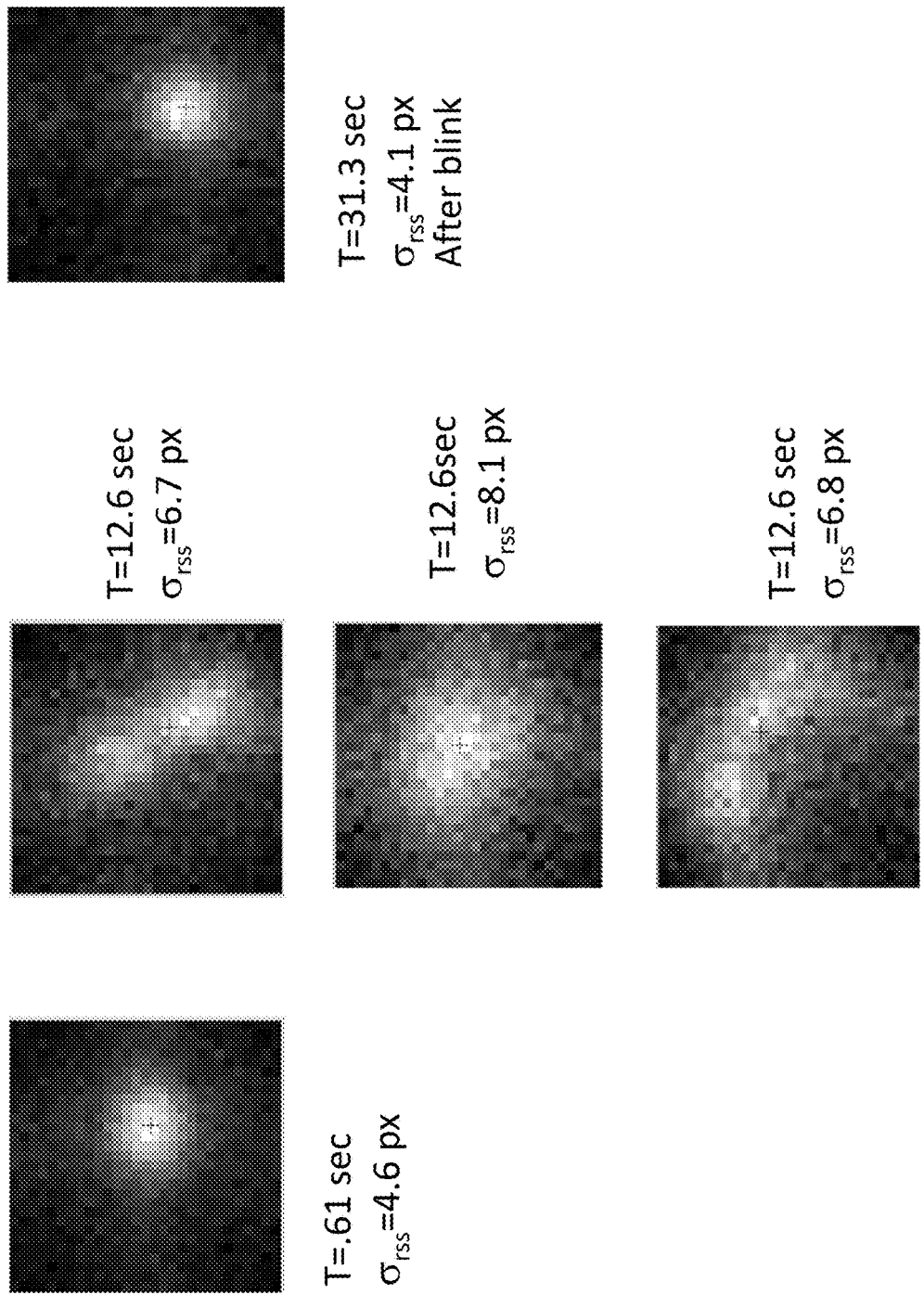
FIG. 18 illustrates wavefront sensor spot degradation as a function of time after a blink for an example eye.

FIG. 18 illustrates wavefront sensor spot degradation as a function of time after a blink for an example eye.

Figure 19:
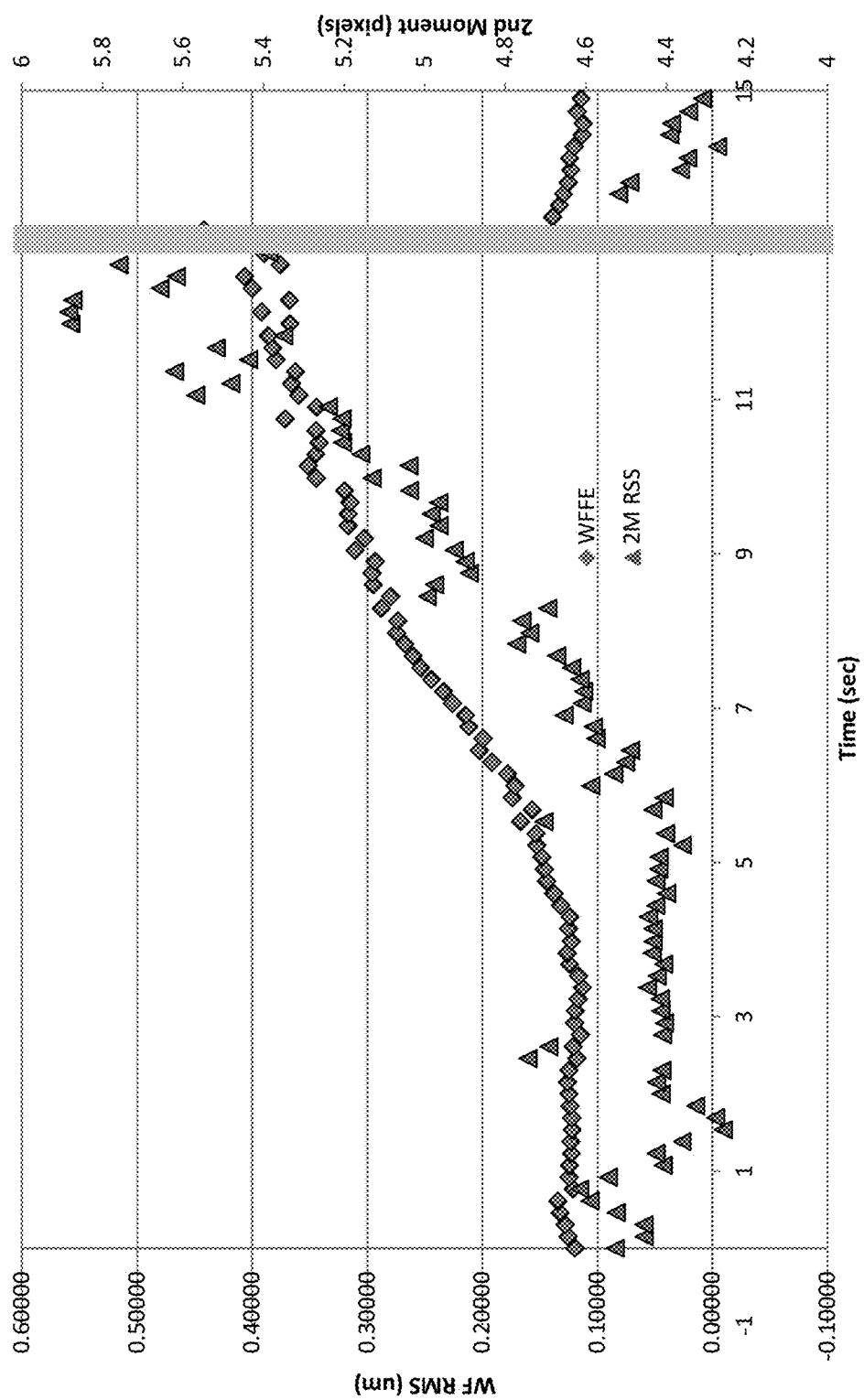
FIG. 19 illustrates how the $2^{nd}$ moment RSS spot size as a function of time correlates with wavefront fit error for an example eye.

FIG. 19 illustrates how the $2^{nd}$ moment RSS spot size as a function of time correlates with wavefront fit error for an example eye. Again, the thick vertical bar represents a time interval during which a blink occurred.

Figure 20:
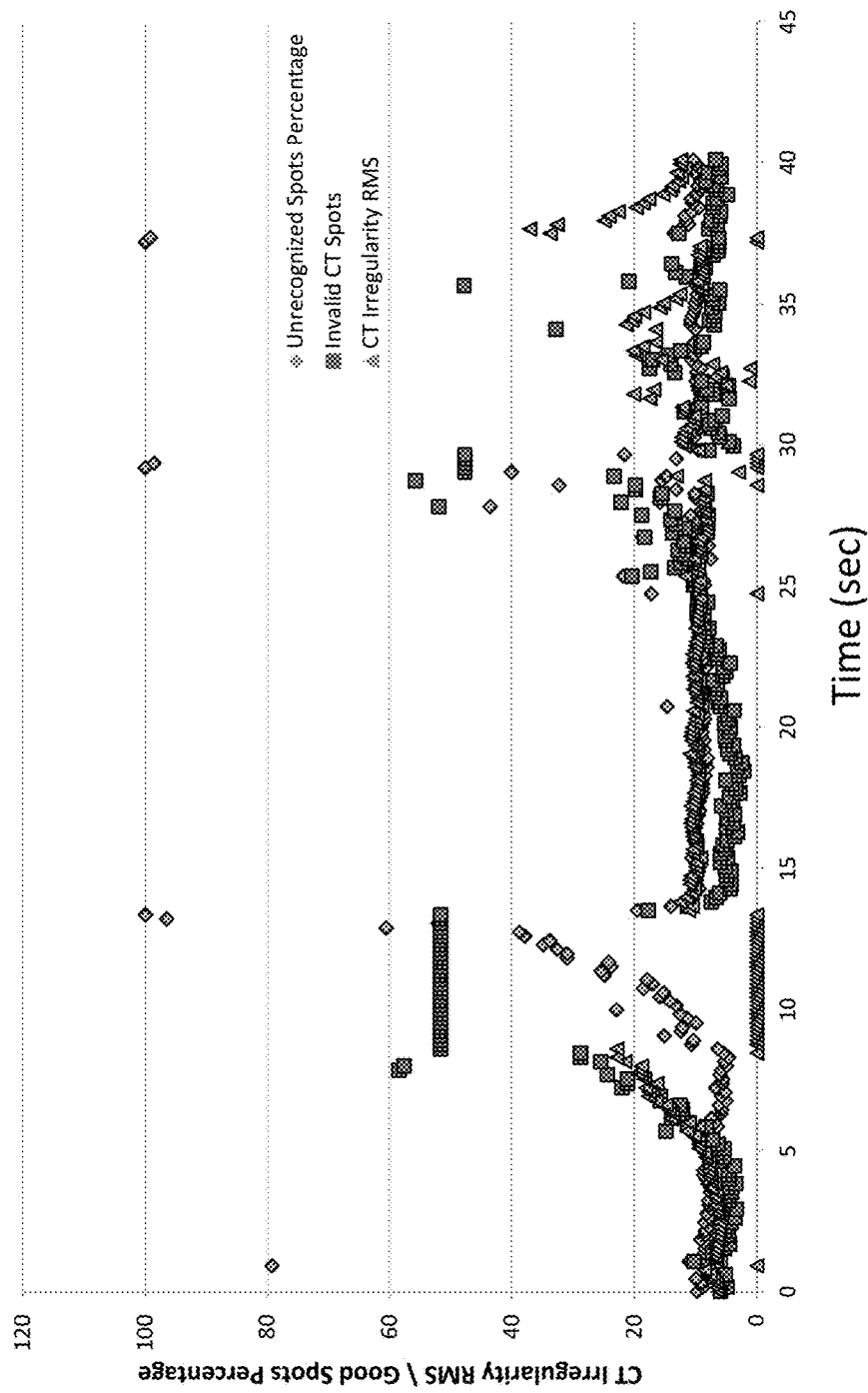
FIG. 20 illustrates how the percentage of bad corneal topography spots as a function of time correlates with RMS irregularity in the measured corneal topography as a function of tie for an example eye.

FIG. 20 illustrates how the percentage of bad corneal topography spots as a function of time correlates with RMS irregularity in the measured corneal topography as a function of tie for an example eye.

Figure 21B:
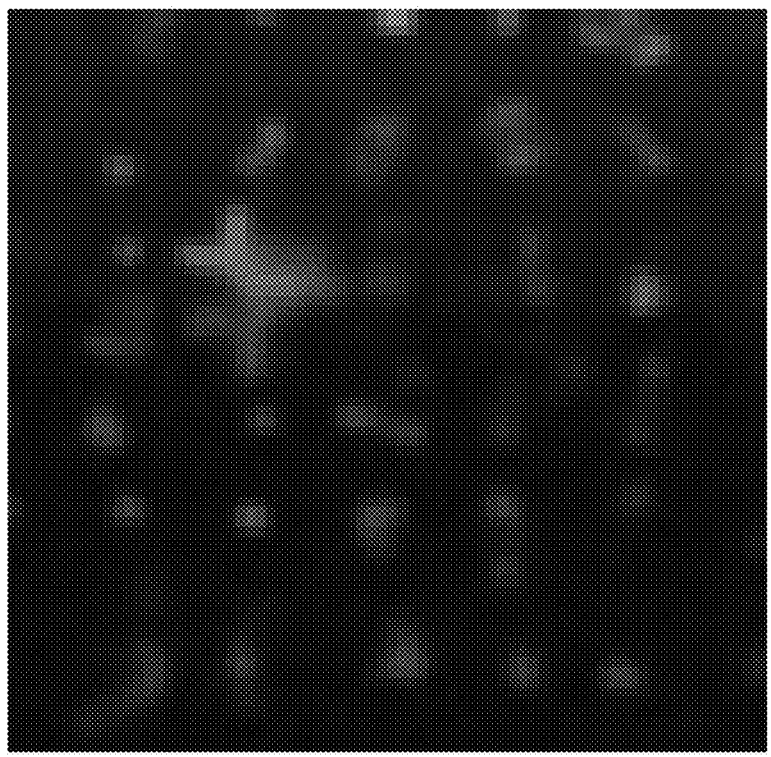
FIGS. 21A and 21B illustrate degradation of corneal topography spots in a localized corneal region of an example eye due to tear film breakup.
Figure 21A:
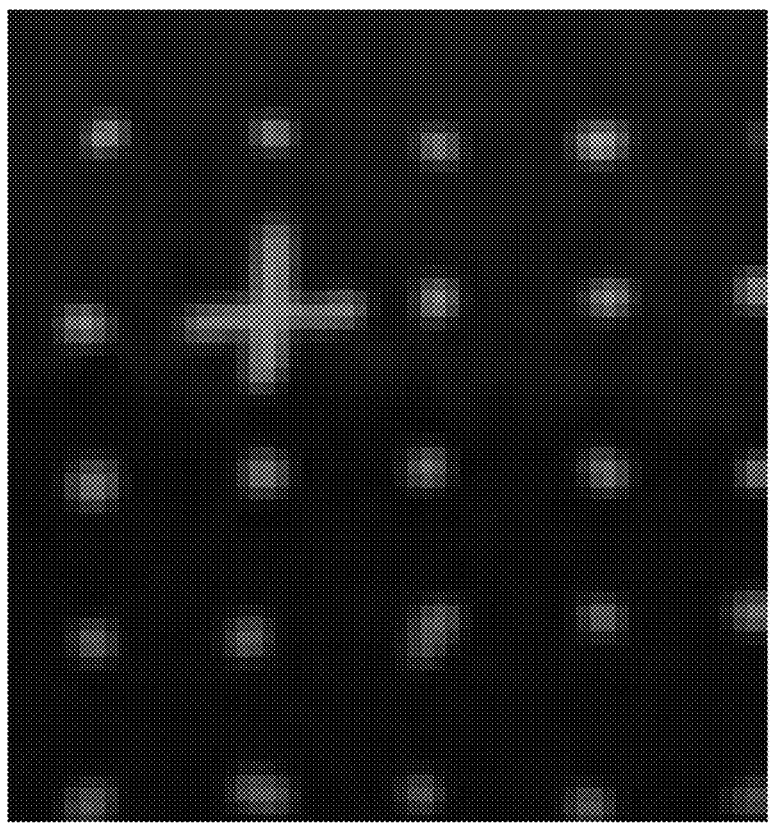

FIGS. 21A and 21B illustrate degradation of corneal topography (CT) spots in a localized corneal region of an example eye due to tear film breakup. In FIGS. 21A and 21B, each CT spot represents a region ~0.2 mm×0.2 mm. Locally rough or irregular surfaces result in spot image breakup. Degraded spots can be assessed by comparing a pattern recognition score to an ideal spot. FIG. 21 represents a case where the number of "good" spots was 923, indicating an intact tear film, while FIG. 21B represents a case of a deteriorated tear film. The typical number of "bad" spots when a degraded tear film is first observed was 511. The fractional area is just the ratio of the "bad" spots to "total" number of spots.

Figure 22:
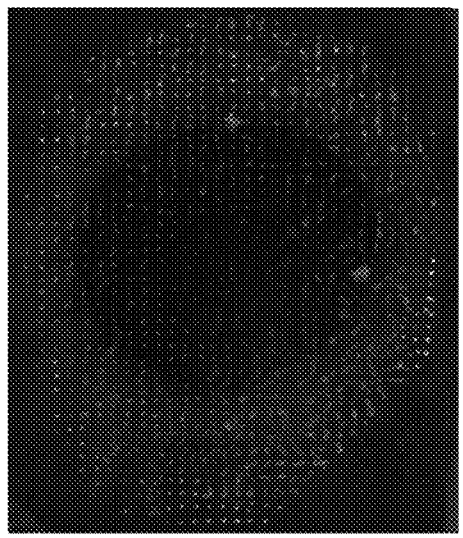
FIG. 22 illustrates degradation of corneal topography spots as a function of time for an example eye due to tear film breakup.
Figure 22:
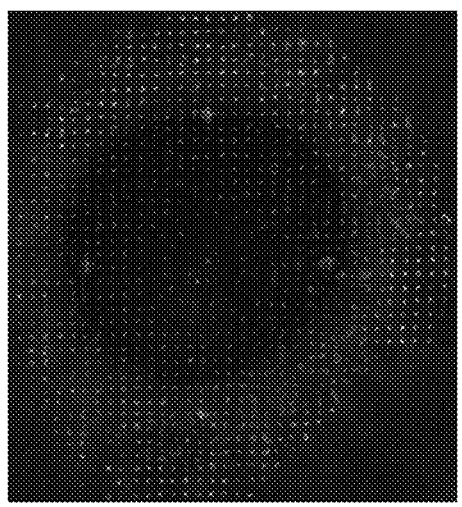
Figure 22:
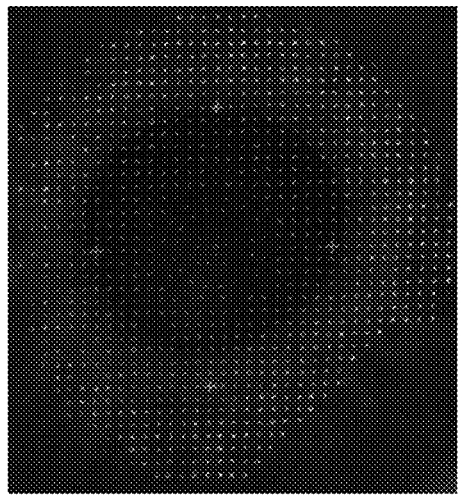
Figure 22:
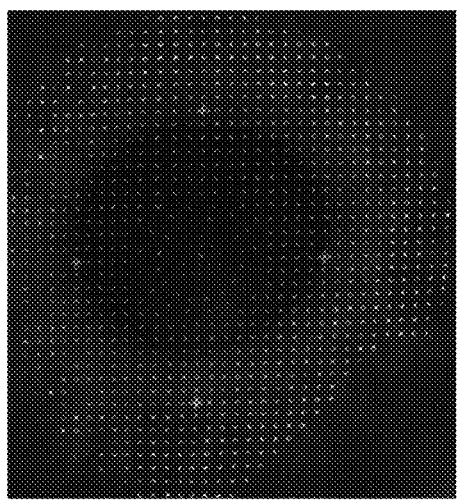

FIG. 22 illustrates degradation of corneal topography spots as a function of time for an example eye due to tear film breakup.

Figure 23:
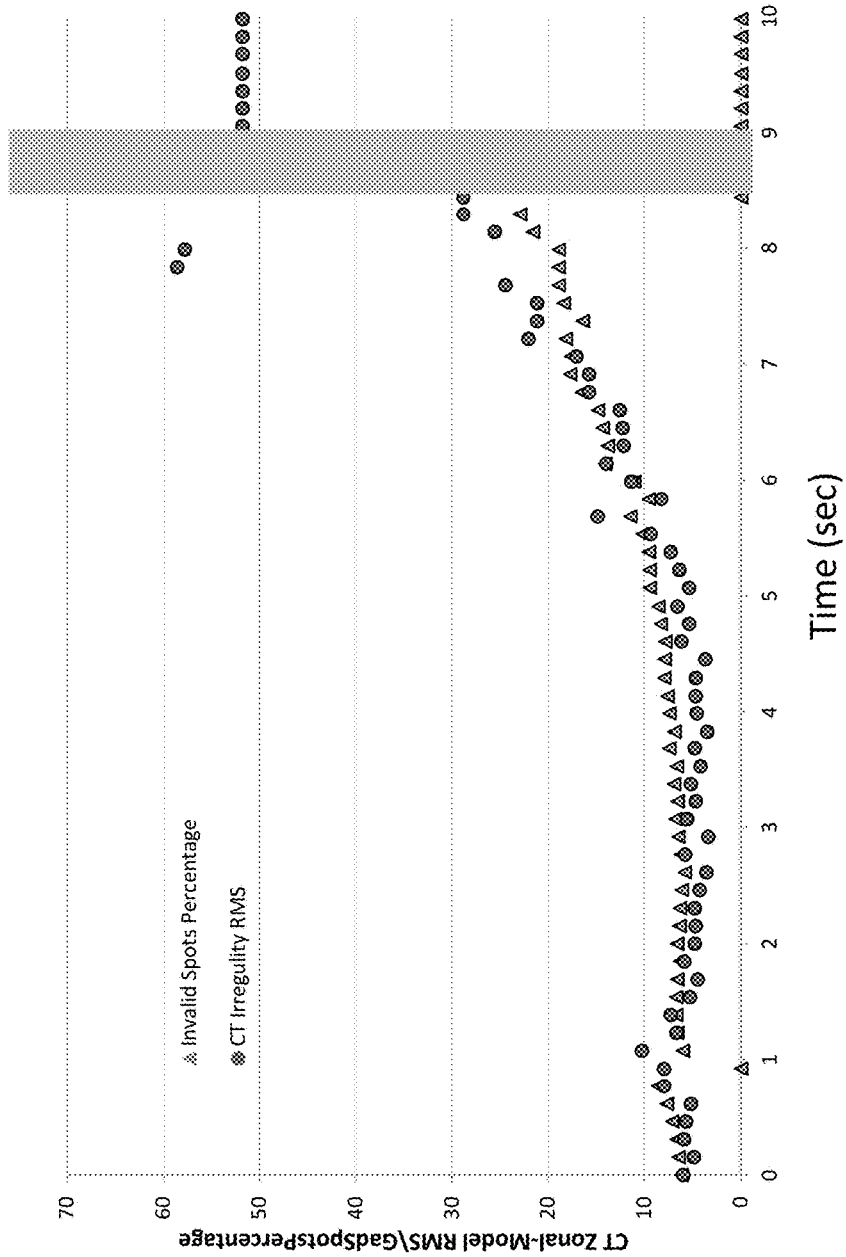
FIG. 23 plots the percentage of invalid corneal topography spots and RMS corneal topography irregularity as a function of time after an initial blink for an example eye.

FIG. 23 plots the percentage of invalid corneal topography spots and RMS corneal topography irregularity as a function of time after an initial blink for an example eye. Again, the thick vertical bar represents a time interval during which a blink occurred.

Figure 24:
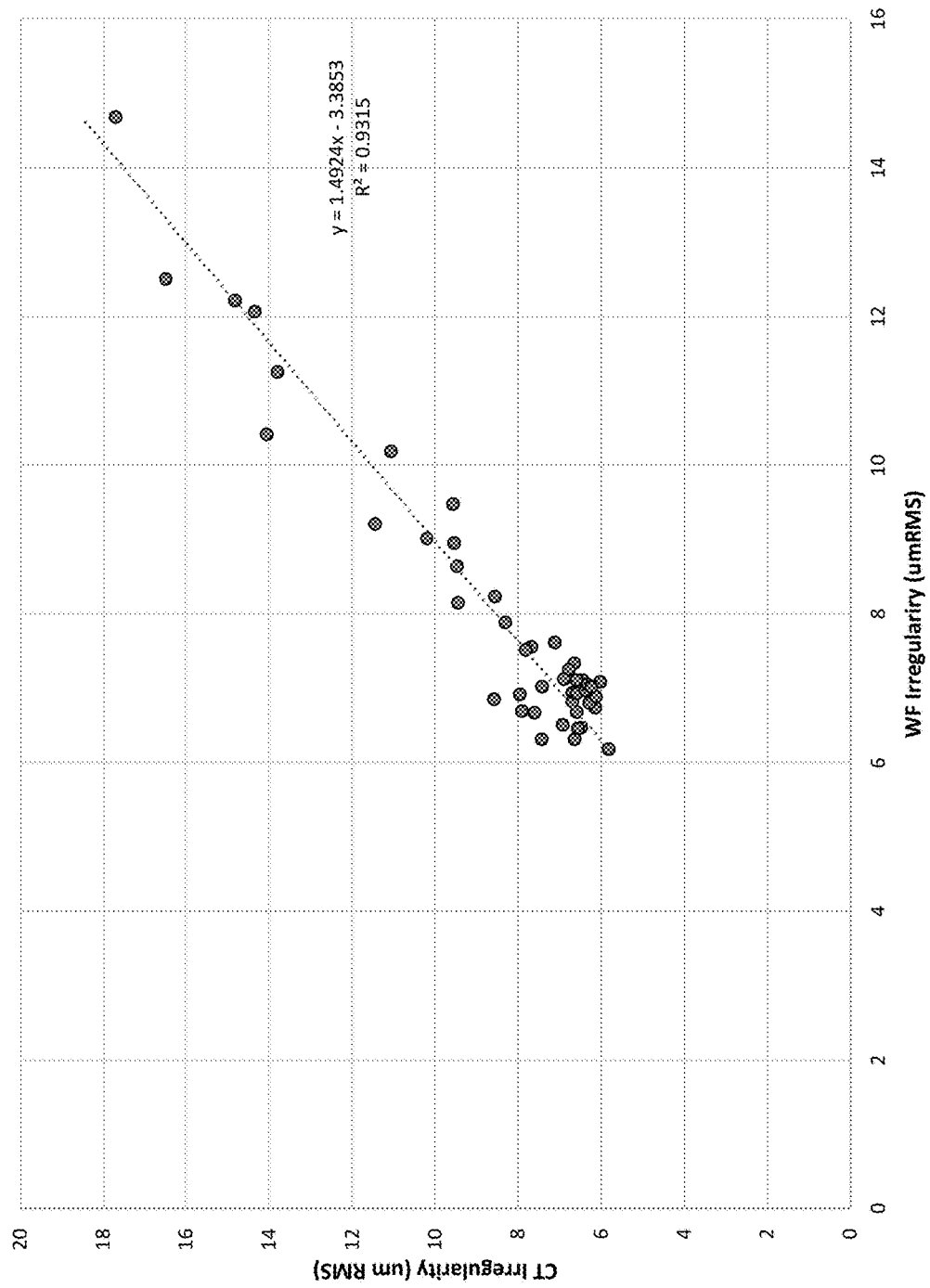
FIG. 24 shows the correlation of the RMS wavefront fit error and RMS corneal topography irregularity for the time after an initial blink for an example eye.

FIG. 24 plots RMS wavefront fit error and RMS corneal topography irregularity as a function of time after an initial blink for an example eye, before the tear film breaks.

Figure 25:
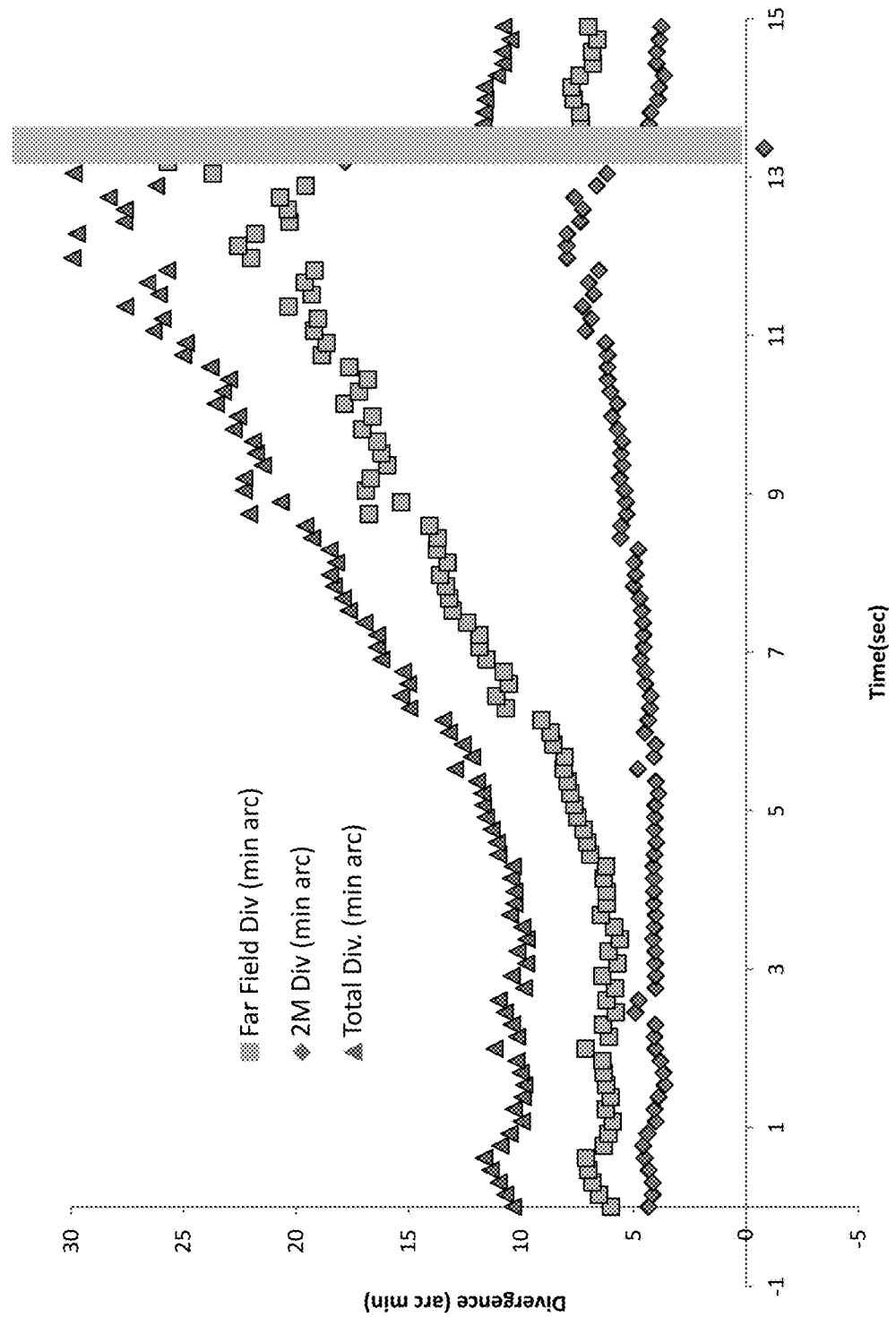
FIG. 25 plots measures of angular divergence for an example eye as a function of time after an initial blink.
Figure 26:
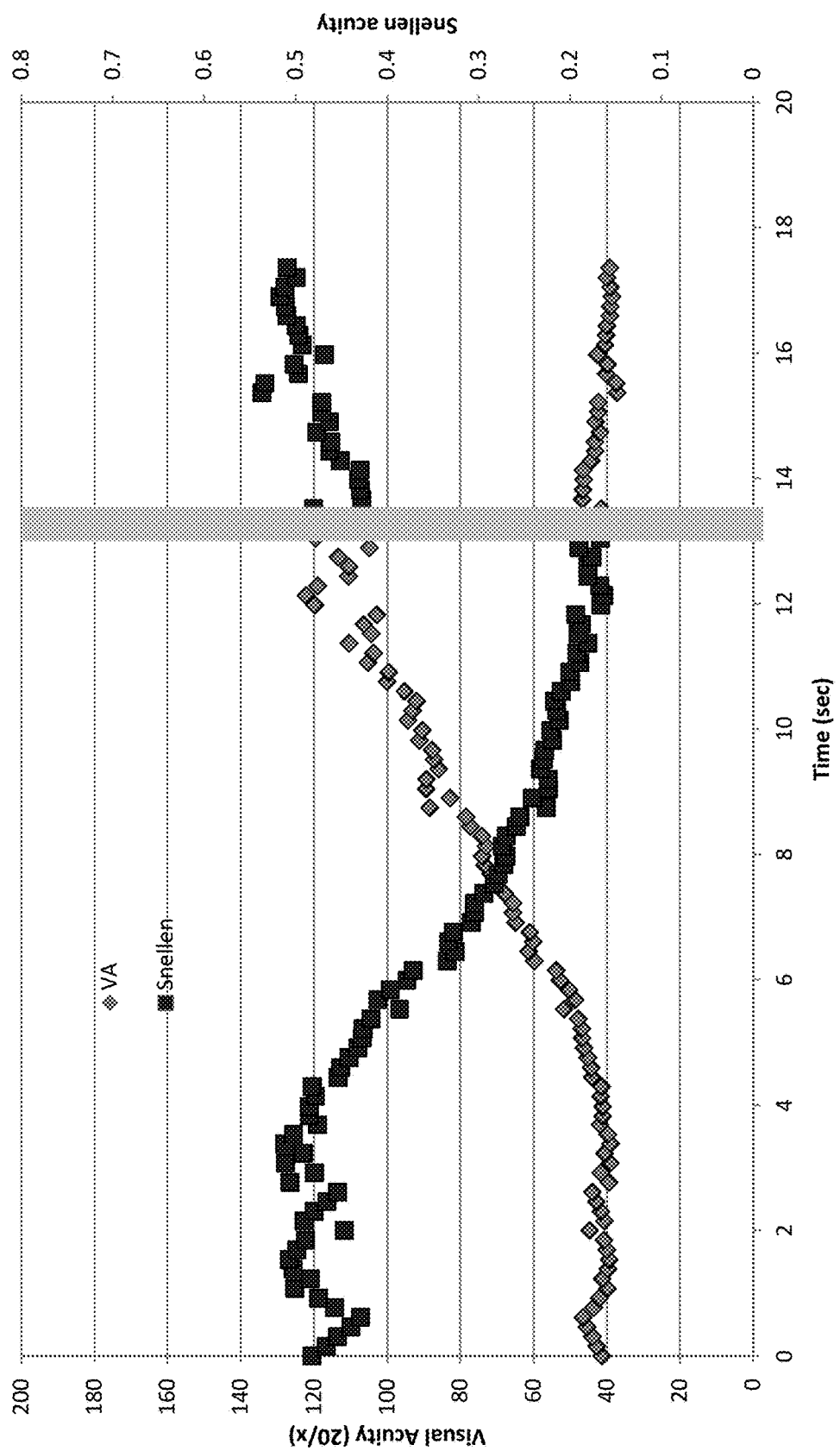
FIG. 26 presents the calculated Snellen acuity and the predicted Visual Acuity (in units of 20/X) for the total divergence shown in FIG. 25

FIG. 25 plots measures of angular divergence for an example eye as a function of time after an initial blink. Angular divergence may be employed as a gauge or predictor of visual acuity (see Keating reference, cited above, for example at page 489). In FIG. 25, the bottom data set represents wavefront detector spot size second moment data; the middle data set represents point spread function data from the entire pupil; and the top data set represents an addition of the bottom data set and the middle data set. This can be used to predict the visual acuity using the Rayleigh criteria or with another method (such as is disclosed in Neal et al. U.S. Pat. No. 6,607,274, which is incorporated herein by reference). This provides the eye care practitioner with a means for objectively comparing tear film to other visual defects. An example of this conversion is presented in FIG. 26, where the Snellen Acuity has been calculated from the angular divergence data of FIG. 25 following the methods of Keating. This is particularly useful for an eye care practitioner, in that the data is now presented in units that can be compared to other metrics of visual acuity. So for a particular patient with some refractive error, some static aberrations and some tear film effects, the ECP can determined that the tear film will contribution a certain percentage of the overall error, and if other errors were corrected, the resulting VA would still be limited to a specific measured value. In FIG. 26 the VA starts at about 20/40 but, as the tear film breaks up, grows to over 20/120. This predictive capability will be very useful in prescribing a course of treatment for the tear film condition. Further details about angular resolution may be found in Wikipedia, https://en.wikipedia.org/wiki/Angular_resolution.

The fractional number of "bad" spots corresponds to the area that has good tear film vs. the total region of interest (may be the full cornea or just the pupil). Since the spot quality is known for each individual spot, the wavefront can be weighted with different types of point-spread-functions in order to determine the overall optical system performance. For example, over the pupil, certain topography regions are determined to be "bad". This information is used to compute the spot divergences from the wavefront corresponding to the topography image. The regions with "good" topography use the wavefront directly. In this way a composite far-field intensity distribution (or composite point-spread-function)

can be created that would better represent the image created by the optical system of the eye. This pattern can then be used to determine Snellen acuity and other optical acuity metrics.

From the data illustrated in FIGS. 11-26, the inventors have appreciated the following. Dynamic corneal topography and wavefront measurement data indicates tear film breakup. In the particular example shown in FIGS. 11-26, then data was acquired at 14 Hz. With the use of faster electronics or higher speed cameras this rate can be increased, limited only by the amount of light that is necessary for a given measurement. As the duty cycle is reduced (shown as 10/30 in the example of FIG. 10), the maximum light level would need to be increased to keep the total amount delivered to the eye constant (for example, following the methods disclosed in Neal et al. U.S. Pat. No. 6,607,274). Some phenomena are well resolved by 14 Hz acquisition. However, it may be advantageous to measure the tear film dynamics at even higher speed. This could be accomplished in a different embodiment using higher speed cameras and electronics.

Different effects may be present in a single blink sequence, but the results are not always consistent after each blink, potentially due to an artifact of the artificial blink sequence. Several metrics correlate well with each other, including the wavefront metrics of WFFE, irregularity, and 2nd moment spot size, and the corneal topography metrics of fractional tear area (e.g., percentage of "bad" spots") and CT irregularity. Resolution can be computed from the points spread function of the wavefront data, with effects present from the LOA, HOA, VHOA, and micro aberrations as illustrated in FIG. 3 above.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

All patents and patent applications cited here are hereby incorporated by reference hereby reference in their entirety.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made and remain within the concept without departing from the spirit or scope of the invention. Such variations would become clear to one of ordinary skill in the art after inspection of the specification, drawings and claims herein. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

We claim:

1. A system, comprising:
a wavefront aberrometer configured to perform a series of wavefront measurements to obtain a plurality of sets of wavefront aberrometry data for an eye, each set of wavefront aberrometry data being obtained at a corresponding different point in time;
a corneal topographer configured to perform a series of corneal topography measurements to obtain a plurality of sets of corneal topography data for the eye, each set of corneal topography data being obtained at a corresponding different point in time; and
a processor configured to process the wavefront aberrometry data and the corneal topography data to produce combined tear film breakup data as a function of time, operative as a metric for evaluating a level of tear film breakup of the eye as a function of time.

2. The system of claim 1, wherein the processor is configured to process the wavefront aberrometry data to produce tear film breakup wavefront data including at least one of wavefront fit error data, wavefront zonal-modal irregularity data, wavefront detector spot size equivalent width data, and wavefront detector spot size second moment data, and point spread function data for the eye as a function of time.

3. The system of claim 2, wherein the processor is configured to process the corneal topography data to produce at least one of tear film breakup corneal topography data, including at least one of corneal topography fit error data, corneal topography zonal-modal irregularity data, corneal topography valid spotsize percentage, and pupil blur fraction data.

4. The system of claim 3, wherein the processor is configured to combine the tear film breakup wavefront data and the tear film breakup corneal topography data to produce the combined tear film breakup data.

5. The system of claim 1, further comprising a controller configured to control the wavefront aberrometer and the corneal topographer to operate in a multiplexed manner to obtain one of the sets of wavefront aberrometry data and one of the sets of corneal topography data in each of a plurality of consecutive time frames.

6. The system of claim 5, wherein the time frame is about 30 milliseconds.

7. The system of claim 1, further comprising a controller configured to control the wavefront aberrometer and to control the corneal topographer such that each of the sets of wavefront aberrometry data is obtained nearly simultaneously with a corresponding one of the sets of corneal topography data.

8. The system of claim 1, wherein the processor is configured to distinguish between different mechanisms of tear film breakup based on at least one of the processed wavefront aberrometry data and the processed corneal topography data.

9. The system of claim 1, wherein the processor is configured to objectively discriminate between optical effects caused by too few tears, and optical effects caused by too much tear liquid, based on the processed wavefront data and the processed corneal topography data.

10. The system of claim 9, wherein the processor is configured to objectively discriminate between different tear states of the eye based on at least one of the processed wavefront aberrometry data and the processed corneal topography data.

11. The system of claim 1, wherein the processor is configured to process the wavefront aberrometry data and the corneal topography data to produce combined tear film breakup data as a function of time by combining an increased sensitivity of the corneal topography data to tear film breakup over a small dynamic range and an increased dynamic range of the wavefront aberrometry data.

12. The system of claim 1, wherein the processor is further configured to determine a tear film break up condition objectively by correlation of two or more of: wavefront irregularity, average 2nd moment spot size of wavefront spots, wavefront spot distortion, a number of bad corneal topography spots, a fraction of bad corneal topography spots, and point spread function angular divergence.

13. The system of claim 1, further comprising an optical coherence tomographer configured to perform a series of corneal topography (OCT) measurements to obtain a plurality of sets of OCT data for the tear film of the eye, wherein the processor is further configured to process the OCT data together with the wavefront data and corneal topography data to obtain a measurement of a thickness of the tear film.

14. A system, comprising:
a wavefront aberrometer configured to perform a series of wavefront measurements to obtain a plurality of sets of wavefront aberrometry data for an eye, each set of wavefront aberrometry data being obtained at a corresponding different point in time; and
a processor configured to process the wavefront aberrometry data to produce wavefront detector spot size second moment data for the eye, and point spread function data for the eye, as a function of time, and to combine the wavefront detector spot size second moment data and the point spread function data to produce wavefront tear film breakup data as a function of time, operative as a metric for evaluating a tear film breakup of the eye as a function of time.

15. The method of claim 14, further comprising determining a tear film break up condition objectively by correlating two or more of: wavefront irregularity, average 2nd moment spot size of wavefront spots, wavefront spot distortion, a number of bad corneal topography spots, a fraction of bad corneal topography spots, and point spread function angular divergence.

16. The method of claim 14, further comprising guiding or prescribing a course of treatment for treating a tear film condition of the eye using the combined tear film breakup data.

17. The method of claim 14, further comprising:
performing a series of corneal topography (OCT) measurements to obtain a plurality of sets of OCT data for the tear film of the eye; and
processing the OCT data together with the wavefront data and corneal topography data to obtain a measurement of a thickness of the tear film.

18. A method, comprising:
performing a series of wavefront measurements to obtain a plurality of sets of wavefront aberrometry data for an eye, each set of wavefront aberrometry data being obtained at a corresponding different point in time;
performing a series of corneal topography measurements to obtain a plurality of sets of corneal topography data for the eye, each set of corneal topography data being obtained at a corresponding different point in time;
processing the wavefront aberrometry data and the corneal topography data to produce combined tear film breakup data as a function of time; and
employing the combined tear film breakup data as a metric for evaluating a level of tear film breakup of the eye as a function of time.

19. The method of claim 18, further including processing the wavefront aberrometry data to produce tear film breakup wavefront data including at least one of wavefront fit error data, wavefront zonal-modal irregularity data, wavefront detector spot size equivalent width data, and wavefront detector spot size second moment data, and point spread function data for the eye as a function of time.

20. The method of claim 19, further including processing the corneal topography data to produce at least one of tear film breakup corneal topography data, including at least one of corneal topography fit error data, corneal topography zonal-modal irregularity data, corneal topography valid spotsize percentage, and pupil blur fraction data.

21. The method of claim 20, further including combining the tear film breakup wavefront data and the tear film breakup corneal topography data to produce the combined tear film breakup data.

22. The method of claim 18, further including obtaining one of the sets of wavefront aberrometry data and one of the sets of corneal topography in each of a plurality of consecutive time frames.

23. The method of claim 22, wherein the time frame is about 30 milliseconds.

24. The method of claim 18, wherein each of the sets of wavefront aberrometry data is obtained nearly simultaneously with a corresponding one of the sets of corneal topography data.

25. The method of claim 18, further comprising distinguishing between different mechanisms of tear film breakup based on at least one of the processed wavefront aberrometry data and the processed corneal topography data.

26. The method of claim 18, further comprising objectively discriminating between optical effects caused by too few tears, and optical effects caused by too much tear liquid, based on the processed wavefront data and the processed corneal topography data.

27. The method of claim 18, further comprising objectively discriminating between different tear states of the eye based on at least one of the processed wavefront aberrometry data and the processed corneal topography data.

28. The method of claim 18, wherein processing the wavefront aberrometry data and the corneal topography data to produce combined tear film breakup data as a function of time includes combining an increased sensitivity of the corneal topography data to tear film breakup over a small dynamic range and an increased dynamic range of the wavefront aberrometry data.

29. A method, comprising:
performing a series of wavefront measurements to obtain a plurality of sets of wavefront aberrometry data for an eye, each set of wavefront aberrometry data being obtained at a corresponding different point in time;
processing the wavefront aberrometry data to produce wavefront detector spot size second moment data for the eye, and point spread function data for the eye, as a function of time; and
combining the wavefront detector spot size second moment data and the point spread function data to produce wavefront tear film breakup data as a function of time.

\* \* \* \* \*